United States Patent
Dycus et al.

(10) Patent No.: US 7,101,372 B2
(45) Date of Patent: *Sep. 5, 2006

(54) VESSEL SEALER AND DIVIDER

(75) Inventors: Sean T. Dycus, Superior, CO (US);
Dax D. Brown, Golden, CO (US);
David Farascioni, Bethel, CT (US);
Michael Primavera, Milford, CT (US);
David Fowler, Raleigh, NC (US)

(73) Assignee: Sherwood Sevices AG, Schaffhausen (CH)

( * ) Notice: Subject to any disclaimer, the term of this patent is extended or adjusted under 35 U.S.C. 154(b) by 158 days.

This patent is subject to a terminal disclaimer.

(21) Appl. No.: 10/472,295

(22) PCT Filed: Apr. 6, 2001

(86) PCT No.: PCT/US01/11340

§ 371 (c)(1),
(2), (4) Date: Sep. 18, 2003

(87) PCT Pub. No.: WO02/080795

PCT Pub. Date: Oct. 17, 2002

(65) Prior Publication Data

US 2004/0082952 A1 Apr. 29, 2004

(51) Int. Cl.
*A61B 18/18* (2006.01)
(52) U.S. Cl. ......................... 606/51; 606/205
(58) Field of Classification Search ............ 606/48–52, 606/205–207
See application file for complete search history.

(56) References Cited

U.S. PATENT DOCUMENTS

| | | | |
|---|---|---|---|
| 371,664 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 2,002,594 A | 5/1935 | Wappler et al. | |
| 2,011,169 A | 8/1935 | Wappler | |
| 2,031,682 A | 2/1936 | Wappler et al. | |
| 2,176,479 A | 10/1939 | Willis | |
| 2,305,156 A | 12/1942 | Grubel | |

(Continued)

FOREIGN PATENT DOCUMENTS

CA 2104423 2/1994

(Continued)

OTHER PUBLICATIONS

Sigel et al. "The Mechanism of Blood Vessel Closure by High Frequency Electrocoagulation" Surgery Gynecology & Obstetrics, Oct. 1965 pp. 823-831.

(Continued)

*Primary Examiner*—Michael Peffley

(57) ABSTRACT

An electrosurgical instrument includes a housing having a shaft attached thereto which connects a pair of first and second jaw members such that the jaw members are movable relative to one another to grasp tissue therebetween. The instrument also includes a four-bar handle assembly attached to the housing for actuating a drive rod assembly. The handle assembly includes a handle and a cam-like piston which cooperate to impart a uniform closure pressure against tissue grasped between the jaw members. The instrument also includes a rotating assembly for rotating the jaw members, a knife assembly for separating tissue and a pair of electrical leads connect the jaw members to a source of electrical energy. The electrical leads include slack loops disposed in the rotating assembly which permit rotation of the jaw members about the axis.

10 Claims, 23 Drawing Sheets

U.S. PATENT DOCUMENTS

| | | | |
|---|---|---|---|
| 2,632,661 A | 3/1953 | Cristofv | |
| 2,668,538 A | 2/1954 | Baker | |
| 2,796,065 A | 6/1957 | Kapp | |
| 3,459,187 A | 8/1969 | Pallotta | |
| 3,643,663 A | 2/1972 | Sutter | |
| 3,651,811 A | 3/1972 | Hildenbrandt et al. | |
| 3,862,630 A | 1/1975 | Balamuth | |
| 3,866,610 A | 2/1975 | Kletschka | |
| 3,911,766 A | 10/1975 | Fridolph et al. | |
| 3,920,021 A | 11/1975 | Hiltenbrandt | |
| 3,921,641 A | 11/1975 | Hulka | |
| 3,938,527 A | 2/1976 | Rioux et al. | |
| 3,952,749 A | 4/1976 | Fridolph et al. | |
| 4,005,714 A | 2/1977 | Hiltebrandt | |
| 4,074,718 A | 2/1978 | Morrison, Jr. | |
| 4,088,134 A | 5/1978 | Mazzariello | |
| 4,165,746 A | 8/1979 | Burgin | |
| 4,300,564 A | 11/1981 | Furihata | |
| 4,370,980 A | 2/1983 | Lottick | |
| 4,416,276 A | 11/1983 | Newton et al. | |
| 4,452,246 A | 6/1984 | Bader et al. | |
| 4,492,231 A | 1/1985 | Auth | |
| 4,552,143 A | 11/1985 | Lottick | |
| 4,574,804 A | 3/1986 | Kurwa | |
| 4,597,379 A | 7/1986 | Kihn et al. | |
| 4,600,007 A | 7/1986 | Lahodny et al. | |
| 4,657,016 A | 4/1987 | Garito et al. | |
| 4,662,372 A | 5/1987 | Sharkany et al. | |
| 4,671,274 A | 6/1987 | Sorochenko | |
| 4,685,459 A | 8/1987 | Koch et al. | |
| D295,893 S | 5/1988 | Sharkany et al. | |
| D295,894 S | 5/1988 | Sharkany et al. | |
| 4,763,669 A | 8/1988 | Jaeger | |
| 4,827,929 A | 5/1989 | Hodge | |
| 4,887,612 A | 12/1989 | Esser et al. | |
| 4,938,761 A | 7/1990 | Ensslin | |
| 4,985,030 A | 1/1991 | Melzer et al. | |
| 5,007,908 A | 4/1991 | Rydell | |
| 5,026,370 A | 6/1991 | Lottick | |
| 5,099,840 A | 3/1992 | Goble et al. | |
| 5,116,332 A | 5/1992 | Lottick | |
| 5,147,357 A | 9/1992 | Rose et al. | |
| 5,151,102 A | 9/1992 | Kamiyama et al. | |
| 5,176,695 A | 1/1993 | Dulebohn | |
| 5,190,541 A | 3/1993 | Abele et al. | |
| 5,197,964 A | 3/1993 | Parins | |
| 5,215,101 A | 6/1993 | Jacobs et al. | |
| 5,217,457 A | 6/1993 | Delahuerga et al. | |
| 5,217,458 A | 6/1993 | Parins | |
| 5,244,462 A | 9/1993 | Delahuerga et al. | |
| 5,250,047 A | 10/1993 | Rydell | |
| 5,258,006 A | 11/1993 | Rydell et al. | |
| 5,261,918 A | 11/1993 | Phillips et al. | |
| 5,275,615 A | 1/1994 | Rose | |
| 5,277,201 A | 1/1994 | Stern | |
| 5,282,799 A | 2/1994 | Rydell | |
| 5,290,286 A | 3/1994 | Parins | |
| 5,304,203 A | 4/1994 | El-Mallawany et al. | |
| 5,308,357 A | 5/1994 | Lichtman | |
| 5,318,589 A | 6/1994 | Lichtman | |
| 5,324,289 A | 6/1994 | Eggers | |
| 5,330,471 A | 7/1994 | Eggers | |
| 5,334,183 A | 8/1994 | Wuchinich | |
| 5,334,215 A | 8/1994 | Chen | |
| 5,336,221 A | 8/1994 | Anderson | |
| 5,342,359 A | 8/1994 | Rydell | |
| 5,342,381 A | 8/1994 | Tidemand | |
| 5,342,393 A | 8/1994 | Stack | |
| 5,352,222 A | 10/1994 | Rydell | |
| 5,354,271 A | 10/1994 | Voda | |
| 5,356,408 A | 10/1994 | Rydell | |
| 5,366,477 A | 11/1994 | LeMarie, III et al. | |
| 5,383,897 A | 1/1995 | Wholey | |
| 5,389,098 A | 2/1995 | Tsuruta et al. | |
| 5,389,104 A | 2/1995 | Hahnen et al. | |
| 5,391,166 A | 2/1995 | Eggers | |
| 5,391,183 A | 2/1995 | Janzen et al. | |
| 5,403,312 A | 4/1995 | Yates et al. | |
| 5,411,519 A | 5/1995 | Tovey et al. | |
| 5,411,520 A | 5/1995 | Nash et al. | |
| 5,413,571 A | 5/1995 | Katsaros et al. | |
| 5,415,657 A | 5/1995 | Taymor-Luria | |
| 5,423,810 A | 6/1995 | Goble et al. | |
| 5,425,739 A | 6/1995 | Jessen | |
| 5,429,616 A | 7/1995 | Schaffer | |
| 5,431,674 A | 7/1995 | Basile et al. | |
| 5,437,292 A | 8/1995 | Kipshidze et al. | |
| 5,438,302 A | 8/1995 | Goble | |
| 5,441,517 A | 8/1995 | Kensey et al. | |
| 5,443,463 A | 8/1995 | Stern et al. | |
| 5,443,464 A | 8/1995 | Russell et al. | |
| 5,443,480 A | 8/1995 | Jacobs et al. | |
| 5,445,638 A | 8/1995 | Rydell et al. | |
| 5,445,658 A | 8/1995 | Durrfeld et al. | |
| 5,451,224 A | 9/1995 | Goble et al. | |
| 5,456,684 A | 10/1995 | Schmidt et al. | |
| 5,458,598 A | 10/1995 | Feinberg et al. | |
| 5,460,629 A | 10/1995 | Shlain et al. | |
| 5,462,546 A | 10/1995 | Rydell | |
| 5,472,443 A | 12/1995 | Cordis et al. | |
| 5,478,351 A | 12/1995 | Meade et al. | |
| 5,480,409 A * | 1/1996 | Riza | 606/205 |
| 5,484,436 A | 1/1996 | Eggers et al. | |
| 5,496,317 A | 3/1996 | Goble et al. | |
| 5,496,347 A | 3/1996 | Hashiguchi et al. | |
| 5,499,997 A | 3/1996 | Sharpe et al. | |
| 5,509,922 A | 4/1996 | Aranyi et al. | |
| 5,514,134 A | 5/1996 | Rydell et al. | |
| 5,527,313 A | 6/1996 | Scott et al. | |
| 5,531,744 A | 7/1996 | Nardella et al. | |
| 5,536,251 A | 7/1996 | Evard et al. | |
| 5,540,684 A | 7/1996 | Hassler, Jr. | |
| 5,540,685 A | 7/1996 | Parins et al. | |
| 5,540,715 A | 7/1996 | Katsaros et al. | |
| 5,558,672 A | 9/1996 | Edwards et al. | |
| 5,569,241 A | 10/1996 | Edwards | |
| 5,569,243 A | 10/1996 | Kortenbach et al. | |
| 5,571,100 A | 11/1996 | Goble et al. | |
| 5,573,424 A | 11/1996 | Poppe | |
| 5,573,535 A | 11/1996 | Viklund | |
| 5,582,611 A | 12/1996 | Tsuruta et al. | |
| 5,585,896 A | 12/1996 | Yamazaki et al. | |
| 5,590,570 A | 1/1997 | LeMaire, III et al. | |
| 5,603,711 A | 2/1997 | Parins et al. | |
| 5,603,723 A | 2/1997 | Aranyi et al. | |
| 5,626,578 A | 5/1997 | Tihon | |
| 5,626,609 A | 5/1997 | Zvenyatsky et al. | |
| 5,630,833 A | 5/1997 | Katsaros et al. | |
| 5,637,110 A | 6/1997 | Pennybacker et al. | |
| 5,643,294 A | 7/1997 | Tovey et al. | |
| 5,647,869 A | 7/1997 | Goble et al. | |
| 5,647,871 A | 7/1997 | Levine et al. | |
| 5,649,959 A | 7/1997 | Hannam et al. | |
| 5,658,281 A | 8/1997 | Heard | |
| 5,662,667 A | 9/1997 | Knodel | |
| 5,667,526 A | 9/1997 | Levin | |
| 5,674,220 A | 10/1997 | Fox et al. | |
| 5,681,282 A | 10/1997 | Eggers et al. | |
| 5,693,051 A | 12/1997 | Schulze et al. | |
| 5,695,522 A | 12/1997 | LeMaire, III et al. | |
| 5,700,261 A | 12/1997 | Brinkerhoff | |
| 5,702,390 A | 12/1997 | Austin et al. | |
| 5,707,369 A | 1/1998 | Vaitekunas et al. | |
| 5,709,680 A | 1/1998 | Yates et al. | |

| | | | | | | |
|---|---|---|---|---|---|---|
| 5,716,366 A | 2/1998 | Yates | | 6,179,837 B1 | 1/2001 | Hooven |
| 5,727,428 A | 3/1998 | LeMaire, III et al. | | 6,183,467 B1 | 2/2001 | Shapeton et al. |
| 5,735,848 A | 4/1998 | Yates et al. | | 6,187,003 B1 | 2/2001 | Buysse et al. |
| 5,735,849 A * | 4/1998 | Baden et al. ............... 606/51 | | 6,190,386 B1 | 2/2001 | Rydell |
| 5,743,906 A | 4/1998 | Parins et al. | | 6,193,718 B1 | 2/2001 | Kortenbach et al. |
| 5,755,717 A | 5/1998 | Yates et al. | | 6,206,876 B1 | 3/2001 | Levine et al. |
| 5,766,130 A | 6/1998 | Selmonosky | | 6,206,877 B1 | 3/2001 | Kese et al. |
| 5,766,166 A | 6/1998 | Hooven | | 6,224,593 B1 | 5/2001 | Ryan et al. |
| 5,766,170 A | 6/1998 | Eggers | | 6,228,080 B1 | 5/2001 | Gines |
| 5,769,849 A | 6/1998 | Eggers | | 6,228,083 B1 | 5/2001 | Lands et al. |
| 5,776,128 A | 7/1998 | Eggers | | 6,267,761 B1 | 7/2001 | Ryan |
| 5,776,130 A | 7/1998 | Buysse et al. | | 6,270,508 B1 | 8/2001 | Klieman et al. |
| 5,779,701 A | 7/1998 | McBrayer et al. | | 6,273,887 B1 | 8/2001 | Yamauchi et al. |
| 5,792,137 A | 8/1998 | Carr et al. | | 6,277,117 B1 | 8/2001 | Tetzlaff et al. |
| 5,792,177 A | 8/1998 | Kaseda | | 6,280,458 B1 | 8/2001 | Boche et al. |
| 5,797,938 A | 8/1998 | Paraschac et al. | | 6,283,961 B1 | 9/2001 | Underwood et al. |
| 5,797,958 A | 8/1998 | Yoon | | D449,886 S | 10/2001 | Tetzlaff et al. |
| 5,800,449 A | 9/1998 | Wales | | 6,322,561 B1 | 11/2001 | Eggers et al. |
| 5,810,808 A | 9/1998 | Eggers | | 6,334,860 B1 | 1/2002 | Dorn |
| 5,810,811 A | 9/1998 | Yates et al. | | 6,334,861 B1 | 1/2002 | Chandler et al. |
| 5,814,043 A | 9/1998 | Shapeton | | 6,350,264 B1 | 2/2002 | Hooven |
| 5,820,630 A | 10/1998 | Lind | | 6,352,536 B1 | 3/2002 | Buysse et al. |
| 5,827,271 A | 10/1998 | Buysse et al. | | D457,958 S | 5/2002 | Dycus et al. |
| 5,827,279 A | 10/1998 | Hughett et al. | | D457,959 S | 5/2002 | Tetzlaff et al. |
| 5,827,281 A | 10/1998 | Levin | | 6,398,779 B1 | 6/2002 | Buysse et al. |
| 5,833,690 A | 11/1998 | Yates et al. | | 6,402,747 B1 | 6/2002 | Lindemann et al. |
| 5,843,080 A | 12/1998 | Fleenor et al. | | 6,409,728 B1 | 6/2002 | Ehr et al. |
| 5,849,022 A | 12/1998 | Sakashita et al. | | H2037 H | 7/2002 | Yates et al. |
| 5,853,412 A | 12/1998 | Mayenberger | | 6,419,675 B1 | 7/2002 | Gallo, Sr. |
| 5,876,401 A | 3/1999 | Schulze et al. | | 6,425,896 B1 | 7/2002 | Baltschun et al. |
| 5,891,141 A | 4/1999 | Rydell | | 6,443,970 B1 | 9/2002 | Schulze et al. |
| 5,891,142 A | 4/1999 | Eggers et al. | | 6,451,018 B1 | 9/2002 | Lands et al. |
| 5,893,863 A | 4/1999 | Yoon | | 6,458,128 B1 | 10/2002 | Schulze |
| 5,893,875 A | 4/1999 | O'Connor et al. | | 6,458,130 B1 | 10/2002 | Frazier et al. |
| 5,902,301 A | 5/1999 | Olig | | 6,464,704 B1 | 10/2002 | Schmaltz et al. |
| 5,906,630 A | 5/1999 | Anderhub et al. | | 6,503,248 B1 | 1/2003 | Levine |
| 5,908,420 A | 6/1999 | Parins et al. | | 6,506,189 B1 | 1/2003 | Rittman, III et al. |
| 5,913,874 A | 6/1999 | Berns et al. | | 6,511,480 B1 | 1/2003 | Tetzlaff et al. |
| 5,921,984 A | 7/1999 | Sutcu et al. | | 6,514,251 B1 | 2/2003 | Ni et al. |
| 5,935,126 A | 8/1999 | Riza | | 6,544,264 B1 | 4/2003 | Levine et al. |
| 5,944,718 A | 8/1999 | Austin et al. | | 6,569,162 B1 | 5/2003 | He |
| 5,951,549 A | 9/1999 | Richardson et al. | | 6,585,735 B1 | 7/2003 | Frazier et al. |
| 5,954,720 A | 9/1999 | Wilson et al. | | 6,620,161 B1 | 9/2003 | Schulze et al. |
| 5,976,132 A | 11/1999 | Morris | | 6,679,882 B1 * | 1/2004 | Kornerup ............... 606/51 |
| 5,989,277 A | 11/1999 | LeMaire, III et al. | | 6,682,528 B1 | 1/2004 | Frazier et al. |
| 6,004,335 A | 12/1999 | Vaitekunas et al. | | 6,733,498 B1 | 5/2004 | Paton et al. |
| 6,010,516 A | 1/2000 | Hulka | | 6,743,229 B1 | 6/2004 | Buysse et al. |
| 6,024,741 A | 2/2000 | Williamson, IV et al. | | D496,997 S | 10/2004 | Dycus et al. |
| 6,024,744 A | 2/2000 | Kese et al. | | D499,181 S | 11/2004 | Dycus et al. |
| 6,033,399 A | 3/2000 | Gines | | 6,926,716 B1 | 8/2005 | Baker et al. |
| 6,039,733 A | 3/2000 | Buysse et al. | | 6,929,644 B1 | 8/2005 | Truckai et al. |
| 6,041,679 A | 3/2000 | Slater et al. | | 2002/0107517 A1 | 8/2002 | Witt et al. |
| 6,050,996 A | 4/2000 | Schmaltz et al. | | 2002/0188294 A1 | 12/2002 | Couture et al. |
| 6,053,914 A | 4/2000 | Eggers et al. | | 2003/0018331 A1 | 1/2003 | Dycus et al. |
| 6,053,933 A | 4/2000 | Balazs et al. | | 2003/0069571 A1 | 4/2003 | Treat et al. |
| D424,694 S | 5/2000 | Tetzlaff et al. | | 2003/0078578 A1 | 4/2003 | Truckai Csabe et al. |
| D425,201 S | 5/2000 | Tetzlaff et al. | | 2003/0139741 A1 | 7/2003 | Goble et el. |
| RE36,795 E | 7/2000 | Rydell | | 2003/0139742 A1 | 7/2003 | Wampler et al. |
| 6,083,223 A | 7/2000 | Baker | | 2003/0158549 A1 | 8/2003 | Swanson |
| 6,086,586 A | 7/2000 | Hooven | | 2003/0199869 A1 | 10/2003 | Johnson et al. |
| 6,090,107 A | 7/2000 | Borgmeier et al. | | 2004/0147925 A1 | 7/2004 | Buysse et al. |
| 6,096,031 A | 8/2000 | Mitchell et al. | | 2003/0236325 A1 | 11/2004 | Tetzlaff et al. |
| 6,096,037 A * | 8/2000 | Mulier et al. ............... 606/49 | | 2004/0225288 A1 | 11/2004 | Buysse et al. |
| 6,099,550 A | 8/2000 | Yoon | | 2004/0230189 A1 | 11/2004 | Keppel et al. |
| 6,102,909 A | 8/2000 | Chen et al. | | 2004/0243125 A1 | 12/2004 | Dycus et al. |
| 6,110,171 A | 8/2000 | Rydell | | 2004/0249371 A1 | 12/2004 | Dycus et al. |
| 6,113,596 A | 9/2000 | Hooven et al. | | 2004/0249374 A1 | 12/2004 | Tetzlaff et al. |
| 6,113,598 A | 9/2000 | Baker | | 2004/0250419 A1 | 12/2004 | Sremcich et al. |
| H1904 H | 10/2000 | Yates et al. | | 2004/0254573 A1 | 12/2004 | Dycus et al. |
| 6,126,658 A | 10/2000 | Baker | | 2005/0004564 A1 | 1/2005 | Wham et al. |
| 6,152,923 A | 11/2000 | Ryan | | 2005/0004568 A1 | 1/2005 | Lawes et al. |
| 6,174,309 B1 | 1/2001 | Wrublewski et al. | | 2005/0004570 A1 | 1/2005 | Chapman et al. |
| 6,179,834 B1 | 1/2001 | Buysse et al. | | 2005/0021025 A1 | 1/2005 | Buysse et al. |

| | | | |
|---|---|---|---|
| 2005/0021026 A1 | 1/2005 | Baily | |
| 2005/0021027 A1 | 1/2005 | Shields et al. | |
| 2005/0101951 A1 | 5/2005 | Wham et al. | |
| 2005/0113818 A1 | 5/2005 | Sartor et al. | |
| 2005/0113819 A1 | 5/2005 | Wham et al. | |
| 2005/0149151 A1 | 7/2005 | Orszulak et al. | |

FOREIGN PATENT DOCUMENTS

| | | |
|---|---|---|
| DE | 2415263 | 10/1975 |
| DE | 19608716 | 4/1997 |
| DE | 19751108 | 5/1999 |
| EP | 0 541 930 B1 | 5/1983 |
| EP | 0364216 A1 | 4/1990 |
| EP | 518230 A1 | 12/1992 |
| EP | 0572131 | 12/1993 |
| EP | 0572131 A1 | 12/1993 |
| EP | 584787 A1 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 853922 A1 | 7/1998 |
| EP | 0887046 A3 | 1/1999 |
| EP | 0923907 A1 | 6/1999 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| GB | 2214430 A | 6/1989 |
| JP | 501068 | 9/1984 |
| JP | 502328 | 3/1992 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11244298 A2 | 9/1999 |
| JP | 200350732 A2 | 12/2000 |
| JP | 2000342599 A2 | 12/2000 |
| JP | 2001008944 A2 | 1/2001 |
| JP | 2001029356 A2 | 2/2001 |
| JP | 2001128990 A2 | 5/2001 |
| SU | 401367 | 10/1973 |
| WO | WO 92/06642 | 4/1992 |
| WO | WO 94/08524 A | 4/1994 |
| WO | WO 95/02369 | 1/1995 |
| WO | WO 95/07662 | 3/1995 |
| WO | WO 96/13218 | 9/1996 |
| WO | WO 97/00646 | 1/1997 |
| WO | WO 97/00647 | 1/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 A | 3/1999 |
| WO | WO 99/40857 | 8/1999 |
| WO | WO 99/51158 | 10/1999 |
| WO | WO 99/66850 A | 12/1999 |
| WO | WO 00/24330 | 5/2000 |
| WO | WO 00/41638 | 7/2000 |
| WO | WO 00/53112 | 9/2000 |
| WO | WO 01/17448 A | 3/2001 |
| WO | WO 01/54604 | 8/2001 |
| WO | WO 02/07627 | 1/2002 |
| WO | WO 02/080793 | 10/2002 |
| WO | WO 02/080795 | 10/2002 |
| WO | WO 02/080796 | 10/2002 |
| WO | WO 02/080798 | 10/2002 |
| WO | WO 02/080799 | 10/2002 |
| WO | WO 04/032777 | 4/2004 |
| WO | WO 2004/052221 A1 | 6/2004 |
| WO | WO 2004/082495 A1 | 9/2004 |
| WO | WO 2004/098383 A1 | 11/2004 |

OTHER PUBLICATIONS

Bergdahl et al. "Studies on Coagulation and the Development of an Automatic Computerized Bipolar Coagulator" J.Neurosurg, vol. 75, Jul. 1991, pp 148-151.

Kennedy et al. "High-burst-strength, feedback-controlled bipolar vessel sealing" Surgical Endoscopy (1998) 12: 876-878.

Peterson et al. "Comparison of Healing Process Following Ligation with Sutures and Bipolar Vessel Sealing" Surgical Technology International (2001).

Linehan et al. "A Phase I Study of the LigaSure Vessel Sealing System in Hepatic Surgery" Section of HPB Surger, Washington University School of Medicine, St. Louis MO, Presented at AHPBA, Feb. 2001.

Johnson et al. "Evaluation of the LigaSure Vessel Sealing System in Hemorrhoidectomy" American College of Surgeons (ACS) Clinicla Congress Poster (2000).

Sayfan et al. "Sutureless Closed Hemorrhoidectomy: A New Technique" Annals of Surgery vol. 234 No. 1 Jul. 2001 pp. 21-24.

Heniford et al. "Initial Results with an Electrochemical Bipolar Vessel Sealer" Surgical Endoscopy (2000) 15:799-801.

Heniford et al. "Initial Research and Clinical Results with an Electrothermal Bipolar Vessel Sealer" Oct. 1999.

McLellan et al. "Vessel Sealing for Hemostasis During Pelvic Surgery" Int'l Federation of Gynecology and Obstetrics Figo World Congress 2000, Washington, D.C.

Levy et al. "Use of a New Energy-based Vessel Ligation Device During Vaginal Hysterectomy" Int'l Federation of Gynecology and Obstetrics (FIGO) World Congress, Nov. 1999.

Crawford et al. "Use of the LigaSure Vessel Sealing System In Urologic Cancer Surger" Grand Rounds in Urology 1999 vol. 1 Issue 4 pp. 10-17.

Rothenberg et al. "Use of the LigaSure Vessel Sealing System In Minimally Invasive Surgery In Children" Int'l Pediatric Endosurgery Group (IPEG) 2000.

Palazzo et al. "Randomized clinical trial of Ligasure versus open haemorrholdectomy" British Journal of Surgery 2002, 89, 154-157.

Int'l Search Report PCT/US01/11218.

Int'l Search Report PCT/US99/24869.

Int'l Search Report PCT/US98/18640.

Int'l Search Report PCT/US98/23950.

Carbonell et al., "Comparison of theGyrus PlasmaKinetic Sealer and the ValleyLab LigaSure Device in the Hemostasis of Small, Medium, and Large-Sized Arteries" Carolinas Laparoscopic and Advanced Surgery Program, Carolinas Medical Center, Charlotte, NC, 2003.

"Reducing Needlestick Injuries in the Operating Room" Sales/Product Literature, 2001.

Chung et al., "Clinical Experience of Sutureless Closed Hemorrhoidectomy with LigaSure" Diseases of the Colon & Rectum vol. 46, No. 1 Jan. 1, 2003.

Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.

Paul G. Horgan, "A Novel Technique for Parenchymal Division During Hepatectomy" The American Journal of Surgery, vol. 181, No. 3, Apr. 2001 pp. 236-237.

W. Scott Helton, "LigaSure Vessel Sealing System: Revolutionary Hemostasis Product for General Surgery" Sales/Product Literature, 1999.

Michael Choti, "Abdominoperineal Resection with the LigaSure Vessel Sealing System and LigaSure Atlas 20 cm Open Instrument" Innovations That Work, Jun. 2003.

Craig Johnson, "Use of the LigaSure,Vessel Sealing System in Bloodless Hemorrhoidectomy" Innovations That Work, Mar. 2000.

Muller et al., "Extended Left Hemicolectomy Using the LigaSure Vessel Sealing System" Innovations That Work, Sep. 1999.

Herman et al., "Laparoscopic Intestinal Resection With the LigaSure Vessel Sealing System: A Case Report" Innovations That Work, Feb. 2002.

Carus et al., "Initial Experience With The LigaSure Vessel Sealing System in Abdominal Surgery" Innovations That Work, Jun. 2002.

Levy et al., "Randomized Trial of Suture Versus Electrosurgical Bipolar Vessel Sealing in Vaginal Hysterectomy" Obstetrics & Gynecology, vol. 102, No. 1, Jul. 2003.

Levy et al., "Update on Hysterectomy—New Technologies and Techniques" OBG Management, Feb. 2003.

Barbara Levy, "Use of a New Vessel Ligation Device During Vaginal Hysterectomy" FIGO 2000, Washington, D.C.

McLellan et al., "Vessel Sealing For Hemostasis During Gynecologic Surgery" Sales Product Literature, 1999.

Sengupta et al., "Use of a Computer-Controlled Bipolar Diathemy System in Radical Prostatectomies and Other Open Urological Surgery" ANZ Journal of Surgery (2001) 71.9 pp. 538-540.

E. David Crawford "Use of a Novel Vessel Sealing Technology in Management of the Dorsal Veinous Complex" Sales Product Literature, 2000.

Jarrett et al., "Use of the LigaSure Vessel Sealing System for Peri-Hilar Vessels in Laparoscopic Nephrectomy" Sales Product Literature, 2000.

E. David Crawford "Evaluation of a New Vessel Sealing Device in Urologic Cancer Surgery" Sales Product Literature, 2000.

Joseph Ortenberg "LigaSure System Used in Laparoscopic 1st and 2nd Stage Orchipexy" Innovations That Work, Nov. 2002.

Kole et al., "Laparoscopic Palomo Varicocele Ligation in Children and Adolescents" Pediatric Endosurgery & Innovative Techniques, vol. 6, No. 1, 2002.

PCT/US01/11340, International Search Report.
PCT/US01/11420, International Search Report.
PCT/US02/01890, International Search Report.
PCT/US02/11100, International Search Report.
PCT/US04/03436, International Search Report.
PCT/US04/13273, International Search Report.
PCT/US04/15311, International Search Report.
98944778, International Search Report.
98958575, International Search Report.
04027479, International Search Report.
04027705, International Search Report.
04027314, International Search Report.

"Innovations in Electrosurgery" Sales/Product Literature; Dec. 31, 2000.

LigaSure Vessel Sealing System, the Seal of Confidence in General, Gynecologic, Urologic, and Laparaoscopic Surgery Sales/Product Literature; Jan. , 2004.

Olsson et al. "Radical Cystectomy in Females" Current Surgical Techniques in Urology, vol. 14, Issue 3, 2001.

Dulemba et al. "Use of a Bipolar Electrothermal Vessel Sealer in Laparoscopically Assisted Vaginal Hysterectomy" Sales Product Literature; Jan., 2004.

Johnson et al. "Evaluation of a Bipolar electrothermal Vessel Sealing Device in Hemorrhoidectomy" Sales Product Literature; Jan., 2004.

Int'l Search Report EP 04013772.
Int'l Search Report EP 98958575.7.
US 6,090,109, 07/2000, Lands et al. (withdrawn)
US 6,663,629, 12/2003, Buysse et al. (withdrawn)

* cited by examiner

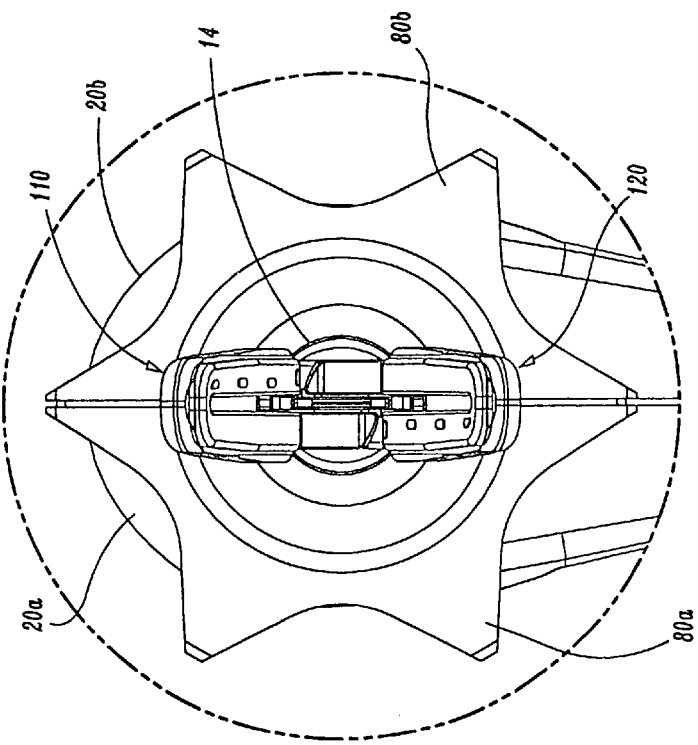
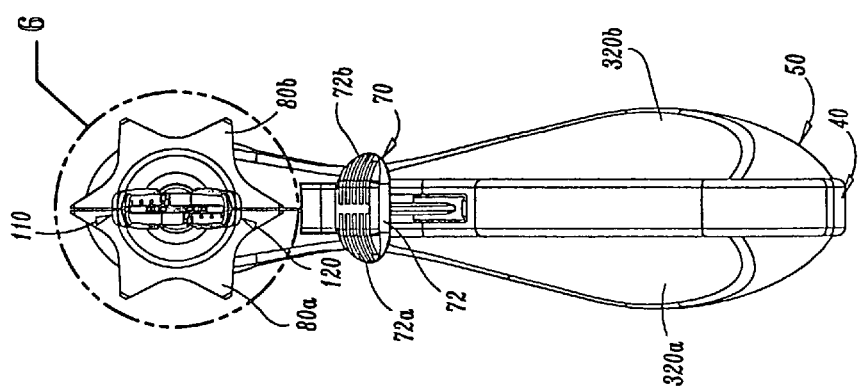

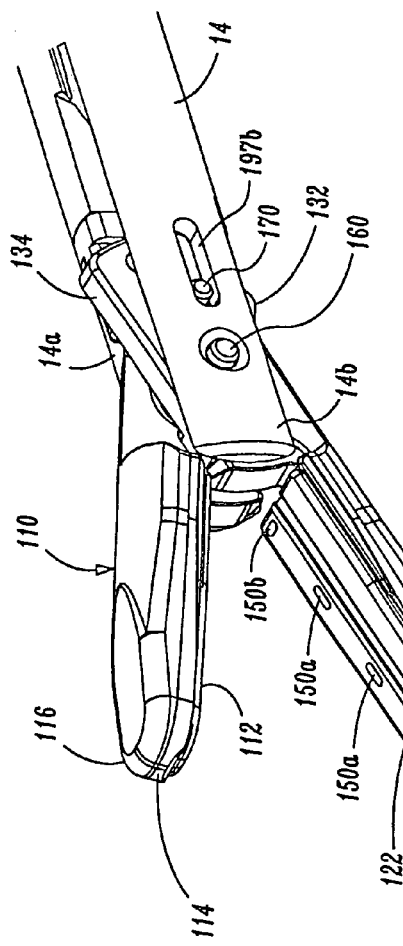
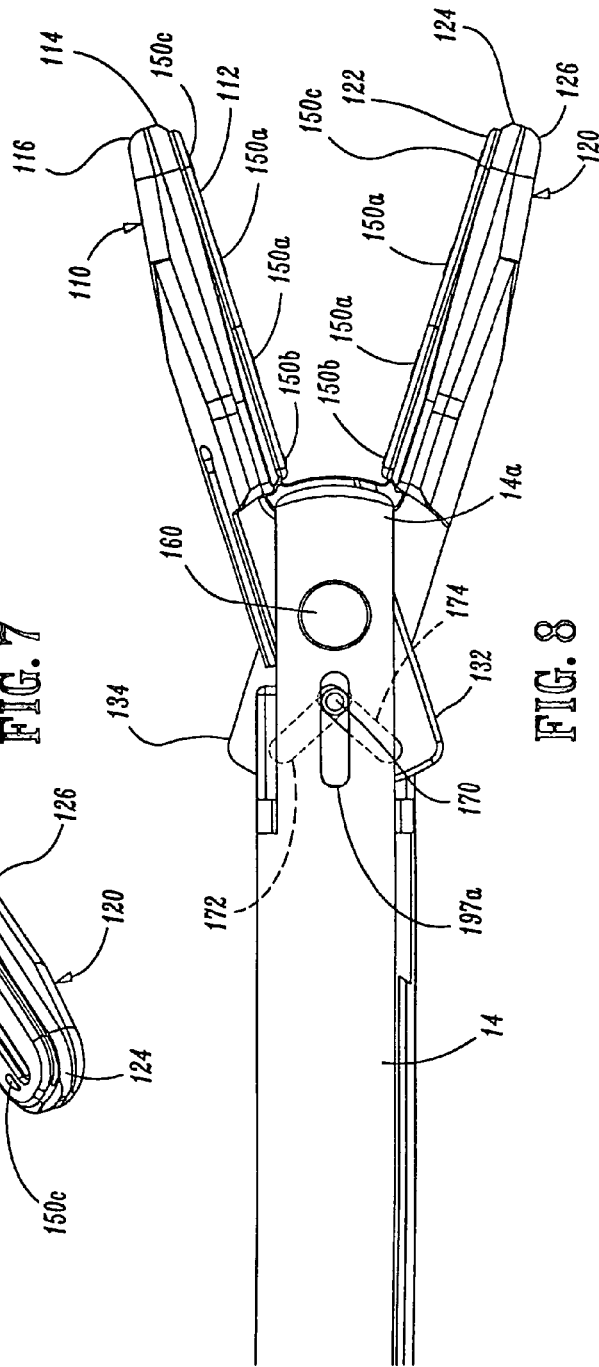
FIG. 7
FIG. 8

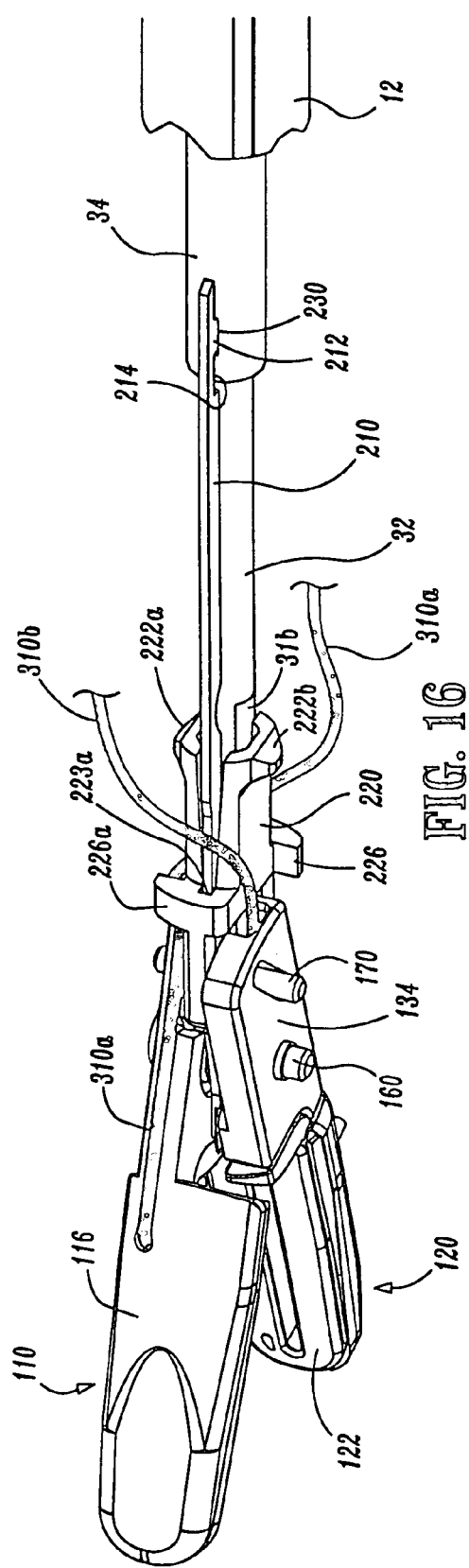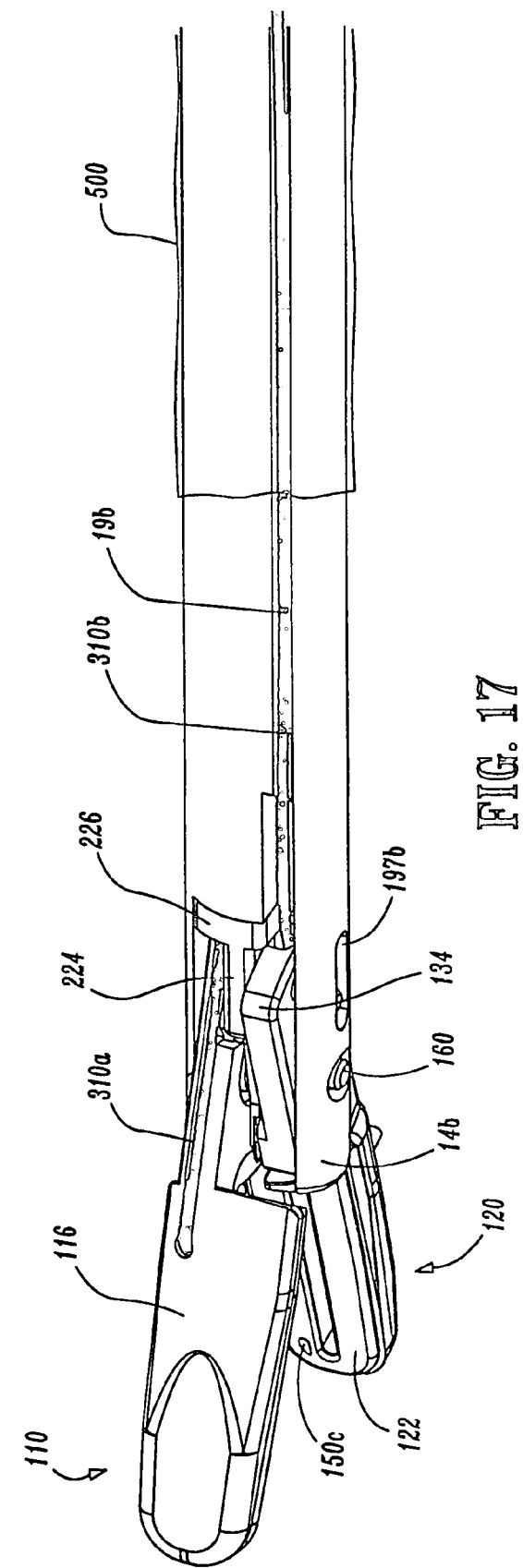

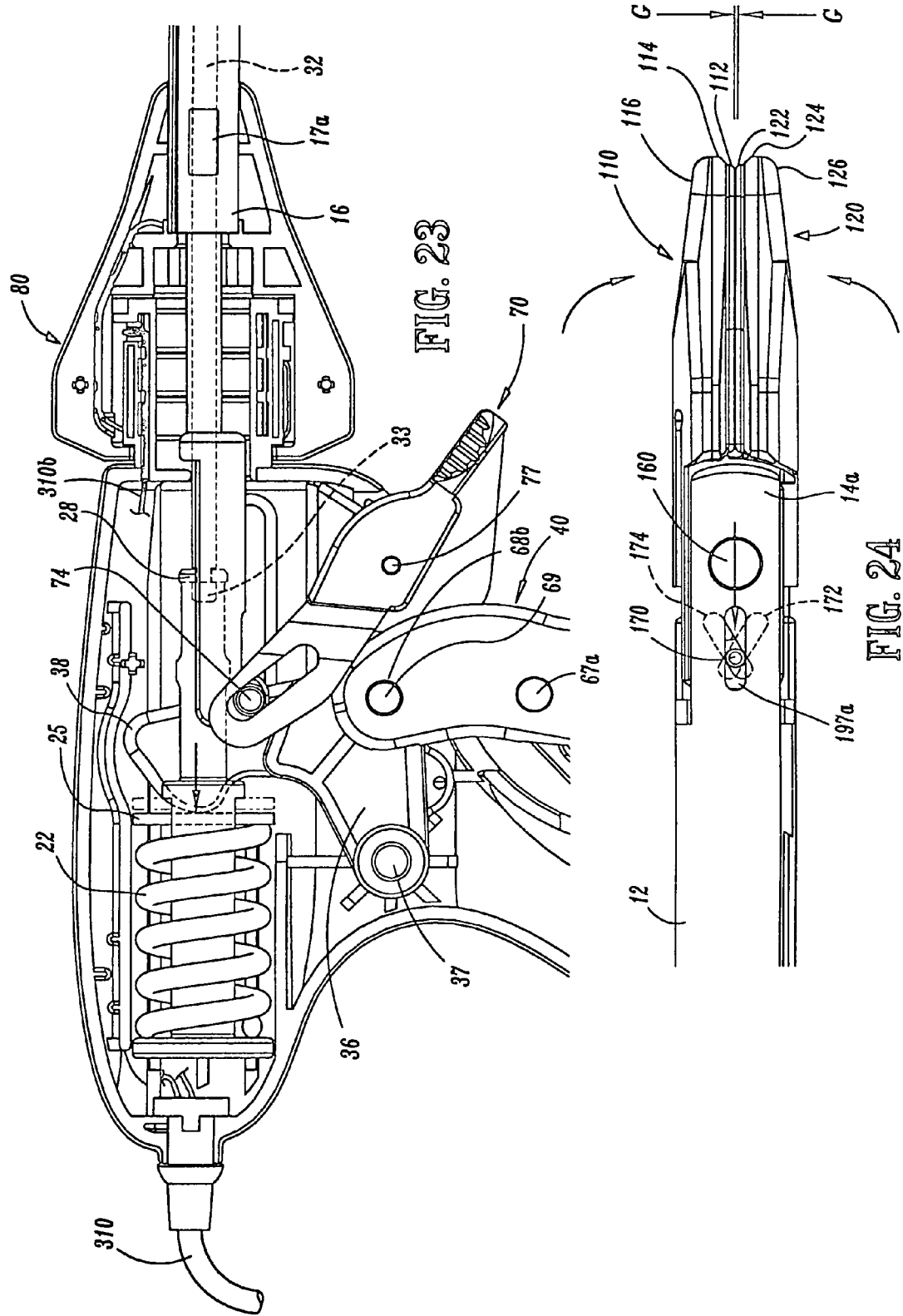

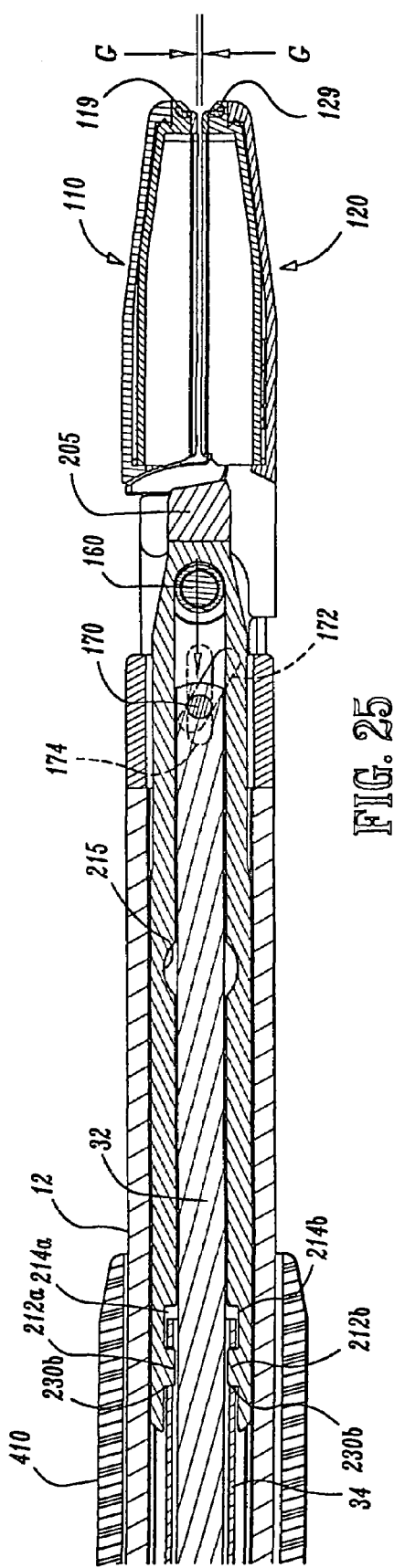
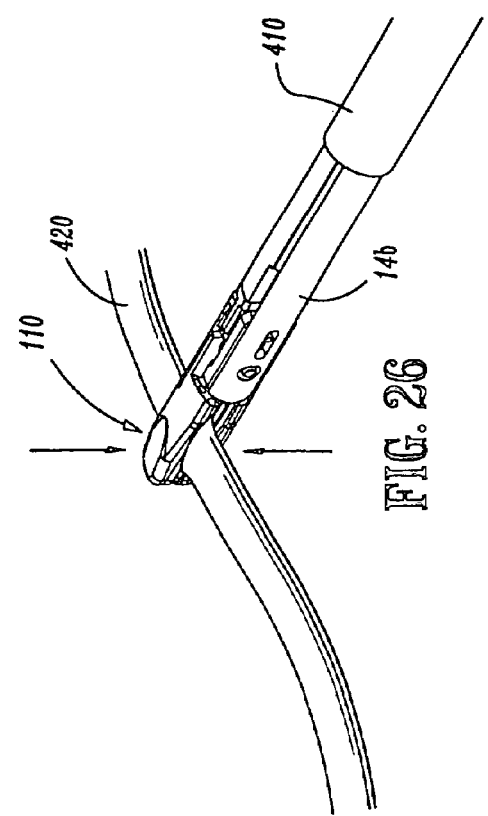
FIG. 25
FIG. 26

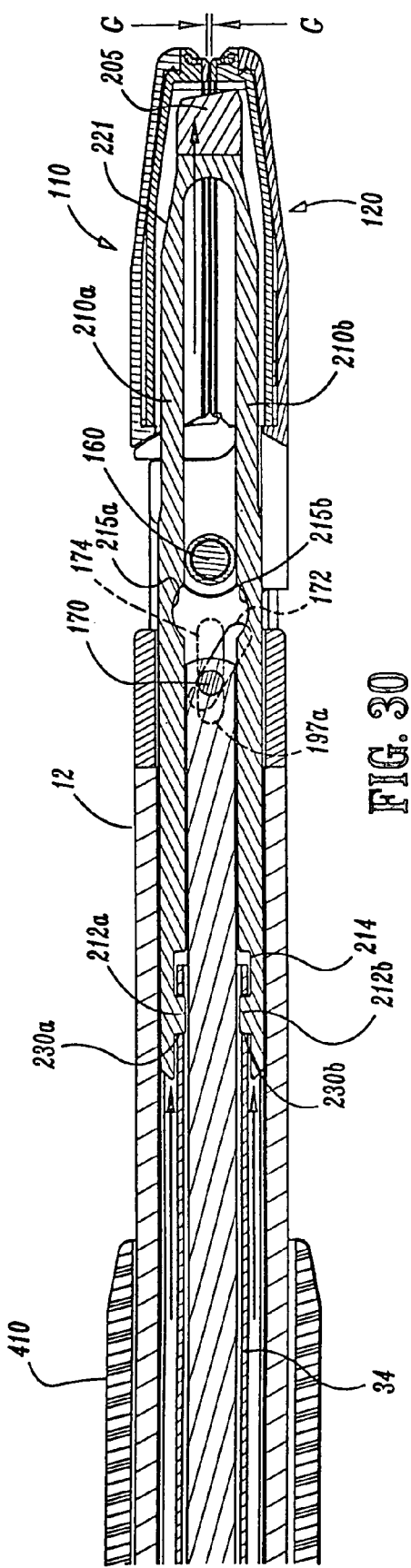

VESSEL SEALER AND DIVIDER

BACKGROUND

The present disclosure relates to an electrosurgical instrument and method for performing endoscopic surgical procedures and more particularly, the present disclosure relates to an open or endoscopic bipolar electrosurgical forceps and method for sealing and/or cutting tissue.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue.

Over the last several decades, more and more surgeons are complimenting traditional open methods of gaining access to vital organs and body cavities with endoscopes and endoscopic instruments which access organs through small puncture-like incisions. Endoscopic instruments are inserted into the patient through a cannula, or port, that has been made with a trocar. Typical sizes for cannulas range from three millimeters to twelve millimeters. Smaller cannulas are usually preferred, which, as can be appreciated, ultimately presents a design challenge to instrument manufacturers who must find ways to make surgical instruments that fit through the cannulas.

Certain endoscopic surgical procedures require cutting blood vessels or vascular tissue. However, due to space limitations surgeons can have difficulty suturing vessels or performing other traditional methods of controlling bleeding, e.g., clamping and/or tying-off transected blood vessels. Blood vessels, in the range below two millimeters in diameter, can often be closed using standard electrosurgical techniques. However, if a larger vessel is severed, it may be necessary for the surgeon to convert the endoscopic procedure into an open-surgical procedure and thereby abandon the benefits of laparoscopy.

Several journal articles have disclosed methods for sealing small blood vessels using electrosurgery. An article entitled *Studies on Coagulation and the Development of an Automatic Computerized Bipolar Coagulator*, J. Neurosurg., Volume 75, July 1991, describes a bipolar coagulator which is used to seal small blood vessels. The article states that it is not possible to safely coagulate arteries with a diameter larger than 2 to 2.5 mm. A second article is entitled *Automatically Controlled Bipolar Electrocoagulation—"COA-COMP"*, Neurosurg. Rev. (1984), pp.187–190, describes a method for terminating electrosurgical power to the vessel so that charring of the vessel walls can be avoided.

As mentioned above, by utilizing an electrosurgical forceps, a surgeon can either cauterize, coagulate/desiccate and/or simply reduce or slow bleeding, by controlling the intensity, frequency and duration of the electrosurgical energy applied through the jaw members to the tissue. The electrode of each jaw member is charged to a different electric potential such that when the jaw members grasp tissue, electrical energy can be selectively transferred through the tissue.

In order to effect a proper seal with larger vessels, two predominant mechanical parameters must be accurately controlled—the pressure applied to the vessel and the gap distance between the electrodes—both of which are affected by the thickness of the sealed vessel. More particularly, accurate application of pressure is important to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical fused vessel wall is optimum between 0.001 and 0.005 inches. Below this range, the seal may shred or tear and above this range the lumens may not be properly or effectively sealed.

With respect to smaller vessel, the pressure applied to the tissue tends to become less relevant whereas the gap distance between the electrically conductive surfaces becomes more significant for effective sealing. In other words, the chances of the two electrically conductive surfaces touching during activation increases as the vessels become smaller.

Electrosurgical methods may be able to seal larger vessels using an appropriate electrosurgical power curve, coupled with an instrument capable of applying a large closure force to the vessel walls. It is thought that the process of coagulating small vessels is fundamentally different than electrosurgical vessel sealing. For the purposes herein, "coagulation" is defined as a process of desiccating tissue wherein the tissue cells are ruptured and dried. Vessel sealing is defined as the process of liquefying the collagen in the tissue so that it reforms into a fused mass. Thus, coagulation of small vessels is sufficient to permanently close them. Larger vessels need to be sealed to assure permanent closure.

U.S. Pat. No. 2,176,479 to Willis, U.S. Pat. Nos. 4,005,714 and 4,031,898 to Hiltebrandt, U.S. Pat. Nos. 5,827,274, 5,290,287 and 5,312,433 to Boebel et al., U.S. Pat. Nos. 4,370,980, 4,552,143, 5,026,370 and 5,116,332 to Lottick, U.S. Pat. No. 5,443,463 to Stern et al., U.S. Pat. No. 5,484,436 to Eggers et al. and U.S. Pat. No. 5,951,549 to Richardson et al., all relate to electrosurgical instruments for coagulating, cutting and/or sealing vessels or tissue. However, some of these designs may not provide uniformly reproducible pressure to the blood vessel and may result in an ineffective or non-uniform seal.

Many of these instruments include blade members or shearing members which simply cut tissue in a mechanical and/or electromechanical manner and are relatively ineffective for vessel sealing purposes. Other instruments rely on clamping pressure alone to procure proper sealing thickness and are not designed to take into account gap tolerances and/or parallelism and flatness requirements which are parameters which, if properly controlled, can assure a consistent and effective tissue seal. For example, it is known that it is difficult to adequately control thickness of the resulting sealed tissue by controlling clamping pressure alone for either of two reasons: 1) if too much force is applied, there is a possibility that the two poles will touch and energy will not be transferred through the tissue resulting in an ineffective seal; or 2) if too low a force is applied the tissue may pre-maturely move prior to activation and sealing and/or a thicker, less reliable seal may be created.

As mentioned above, in order to properly and effectively seal larger vessels, a greater closure force between opposing jaw members is required. It is known that a large closure force between the jaws typically requires a large moment about the pivot for each jaw. This presents a challenge because the jaw members are typically affixed with pins which are positioned to have a small moment arms with respect to the pivot of each jaw member. A large force, coupled with a small moment arm, is undesirable because the large forces may shear the pins. As a result, designers must compensate for these large closure forces by either designing instruments with metal pins and/or by designing instruments which at least partially offload these closure forces to reduce the chances of mechanical failure. As can be appreciated, if metal pivot pins are employed, the metal pins must be insulated to avoid the pin acting as an alternate current path between the jaw members which may prove detrimental to effective sealing.

Increasing the closure forces between electrodes may have other undesirable effects, e.g., it may cause the opposing electrodes to come into close contact with one another which may result in a short circuit and a small closure force may cause pre-mature movement of the issue during compression and prior to activation.

Typically and particularly with respect to endoscopic electrosurgical procedures, once a vessel is sealed, the surgeon has to remove the sealing instrument from the operative site, substitute a new instrument through the cannula and accurately sever the vessel along the newly formed tissue seal. As can be appreciated, this additional step may be both time consuming (particularly when sealing a significant number of vessels) and may contribute to imprecise separation of the tissue along the sealing line due to the misalignment or misplacement of the severing instrument along the center of the tissue sealing line.

Several attempts have been made to design an instrument which incorporates a knife or blade member which effectively severs the tissue after forming a tissue seal. For example, U.S. Pat. No. 5,674,220 to Fox et al. discloses a transparent vessel sealing instrument which includes a longitudinally reciprocating knife which severs the tissue once sealed. The instrument includes a plurality of openings which enable direct visualization of the tissue during the sealing and severing process. This direct visualization allows a user to visually and manually regulate the closure force and gap distance between jaw members to reduce and/or limit certain undesirable visual effects known to occur when sealing vessels, thermal spread, charring, etc. As can be appreciated, the overall success of creating an effective tissue seal with this instrument is greatly reliant upon the user's expertise, vision, dexterity, and experience in judging the appropriate closure force, gap distance and length of reciprocation of the knife to uniformly, consistently and effectively seal the vessel and separate the tissue at the seal along an ideal cutting plane.

U.S. Pat. No. 5,702,390 to Austin et al. discloses a vessel sealing instrument which includes a triangularly-shaped electrode which is rotatable from a first position to seal tissue to a second position to cut tissue. Again, the user must rely on direct visualization and expertise to control the various effects of sealing and cutting tissue.

Thus, a need exists to develop an electrosurgical instrument which effectively and consistently seals and separates vascular tissue and solves many of the aforementioned problems known in the art.

SUMMARY

The present disclosure relates to a bipolar electrosurgical forceps for clamping, sealing and dividing tissue. More particularly, the present disclosure relates to a bipolar electrosurgical forceps which effects consistency in the overall clamping pressure exerted on tissue between opposing jaw members, regulates the gap distances between opposing jaws members, reduces the chances of short circuiting the opposing jaw members during activation, includes non-conductive stop members which assist in manipulating, gripping and holding the tissue prior to and during activation and division of the tissue, and provides a uniquely-designed electrical cable path through the body of the instrument and to the opposing jaw members to reduce the chances of activation irregularities during the manipulation, sealing and dividing of tissue.

The presently-disclosed forceps relates to an electrosurgical instrument for performing sealing and/or dividing tissue and includes a housing having a shaft attached thereto which defines a longitudinal axis and a first jaw member which is movable relative to a second jaw member. Preferably, the first jaw member is attached to the shaft and moves from a first open position wherein the jaw members are disposed in spaced relation relative to one another to a second closed position wherein the jaw members cooperate to grasp tissue therebetween.

The instrument also includes a drive rod assembly which imparts movement of the jaw members between the first and second positions, a rotating assembly which rotates the jaw members about the longitudinal axis and a knife assembly which separates the tissue grasped between the jaw members. A four-bar handle assembly is also included which includes a handle and a cam-like piston which cooperate to impart a uniform closure pressure against the tissue grasped between the jaw members. A pair of electrical leads connect the jaw members to a source of electrical energy and include slack loops disposed in the rotating assembly which permit rotation of the jaw members about the longitudinal axis.

In one embodiment, the first and second jaw members are movable relative to one another in a pivotable fashion and are rotatable substantially 360 degrees about the longitudinal axis. Preferably, the handle and the cam member of the four-bar mechanical linkage cooperate with a spring to create the uniform closure pressure against tissue grasped between the jaw members.

In another embodiment, the handle is lockable within the housing to selectively lock the jaw members relative to one another. Preferably, the knife assembly is variable from a locked configuration to an unlocked configuration upon movement of the four-bar mechanical linkage. For example, the handle may includes a flange which is reciprocated into a channel having predefined internal dimensions disposed within the housing. The flange is dimensioned to cooperate with the predefined internal dimensions of the channel to selectively lock the jaw members relative to one another and unlock the knife assembly.

In yet another embodiment, one of the jaw members includes a longitudinal channel at least partially defined therethrough which permits reciprocation of the knife assembly along an ideal cutting plane to separate tissue. In another embodiment, the rotating assembly includes a mechanical interface, e.g., detent, which cooperates with a corresponding mechanical interface, e.g., notch, disposed on the housing to prevent overrotation of the jaw members.

BRIEF DESCRIPTION OF THE DRAWINGS

Various embodiments of the subject instrument are described herein with reference to the drawings wherein:

FIG. 5 is a front view of the forceps of FIG. 1;

FIGS. 6 is an enlarged view of the indicated area of detail of FIG. 5 showing an enhanced view of the end effector assembly detailing a pair of opposing jaw members;

FIG. 7 is an enlarged, left perspective view of the indicated area of detail of FIG. 1 showing another enhanced view of the end effector assembly;

FIG. 8 is an enlarged, right side view of the indicated area of detail of FIG. 3 with a pair of cam slots of the end effector assembly shown in phantom;

FIG. 16 is an enlarged, top perspective view of the end effector assembly showing the feed path for the electrical cable through the opposing jaw members and the proximal attachment of the knife assembly to a longitudinally-reciprocating knife tube disposed within the shaft;

FIG. 17 is an enlarged, top perspective view of the end effector assembly showing the feed path for the electrical cable along a longitudinally-disposed channel defined within the outer periphery of the shaft;

FIG. 23 is a greatly-enlarged, side view showing the resulting compression movement of a coil spring in reaction to the movement of the four-bar handle assembly;

FIG. 24 is a greatly-enlarged, side view showing the proximal movement of a cam-like drive pin of the end effector assembly as a result of the proximal compression of the coil spring of FIG. 23 which, in turn, moves the opposing jaw members into a closed configuration;

FIG. 25 is a greatly-enlarged, cross-section showing the knife assembly poised for activation within a cannula;

FIG. 26 is a top perspective view showing the opposing jaw members in closed configuration with a tubular vessel compressed therebetween;

FIG. 30 is a greatly-enlarged, cross-section of the distal end of the instrument showing longitudinal reciprocation of the knife assembly upon activation of the trigger assembly;

FIG. 31 is a longitudinal cross-section of the tubular vessel after reciprocation of the knife assembly through the sealing site along preferred cutting line "B—B" of FIG. 28.

DETAILED DESCRIPTION

Figure 20:
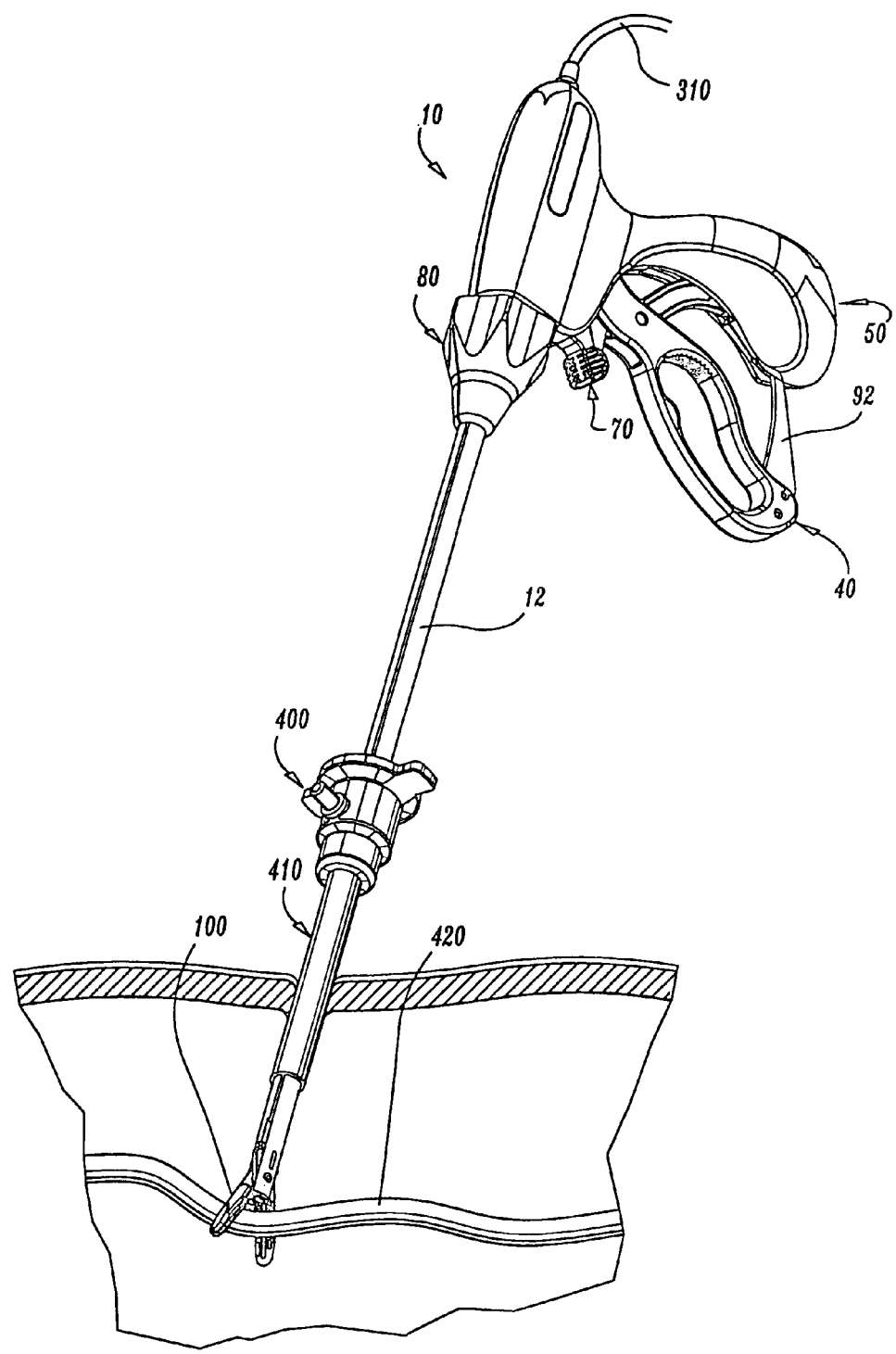
FIG. 20 is a perspective view of the forceps of the present disclosure shown in position to grasp and seal a tubular vessel or bundle through a cannula.

Referring now to FIGS. 1–6, one embodiment of a bipolar forceps 10 is shown for use with various surgical procedures and generally includes a housing 20, a handle assembly 30, a rotating assembly 80, a trigger assembly 70 and an end effector assembly 100 which mutually cooperate to grasp, seal and divide tubular vessels and vascular tissue 420 (FIG. 20). Although the majority of the figure drawings depict a bipolar forceps 10 for use in connection with endoscopic surgical procedures, an open forceps 10' is also contemplated for use in connection with traditional open surgical procedures and is shown by way of example in FIG. 1A. For the purposes herein, the endoscopic version is discussed in detail, however, it is contemplated that open forceps 10' also includes the same or similar operating components and features as described below.

Figure 11:
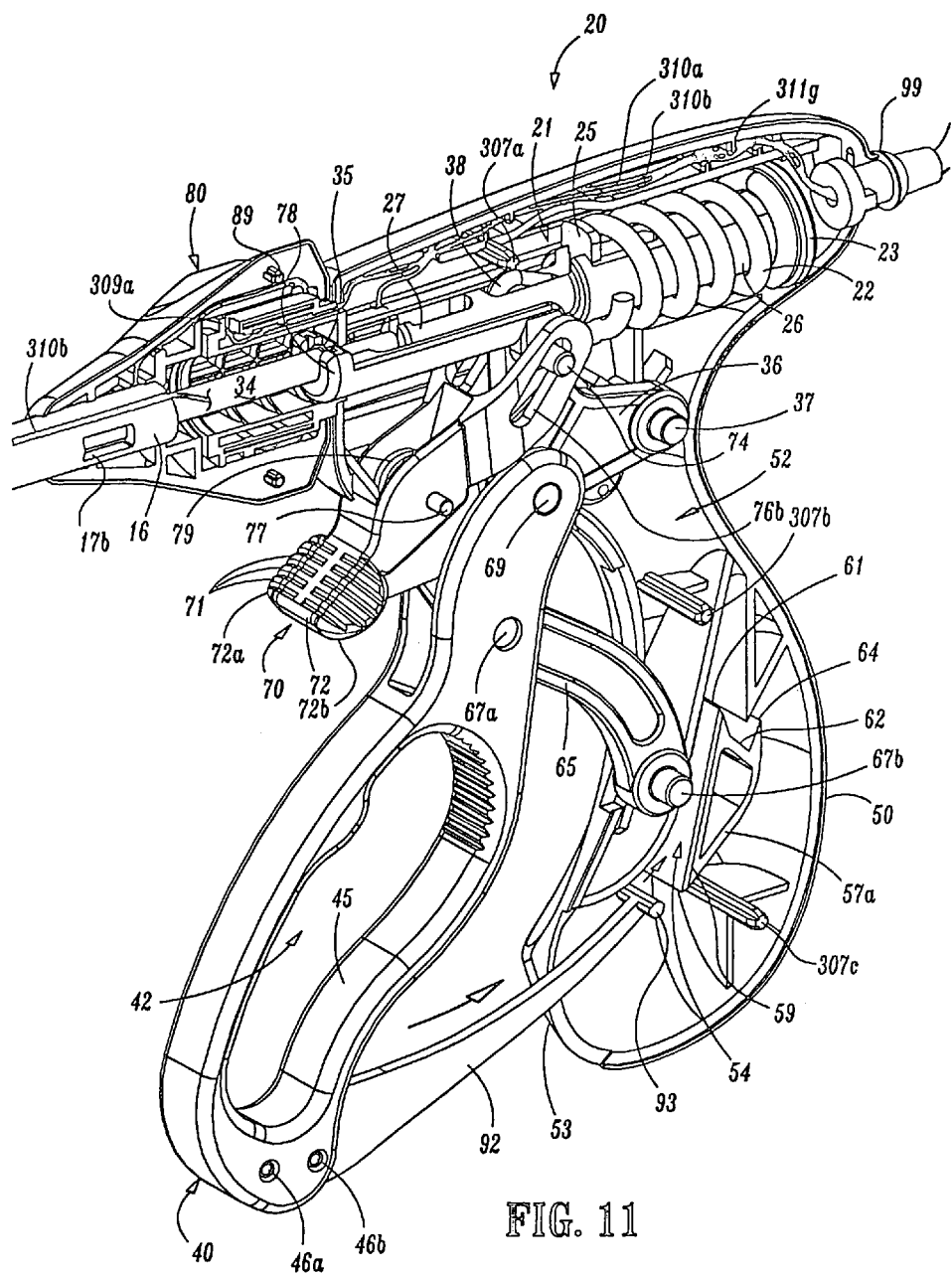
FIG. 11 is an enlarged, left perspective view showing the housing without a cover plate and the internal working components of the forceps disposed therein.
Figure 12:
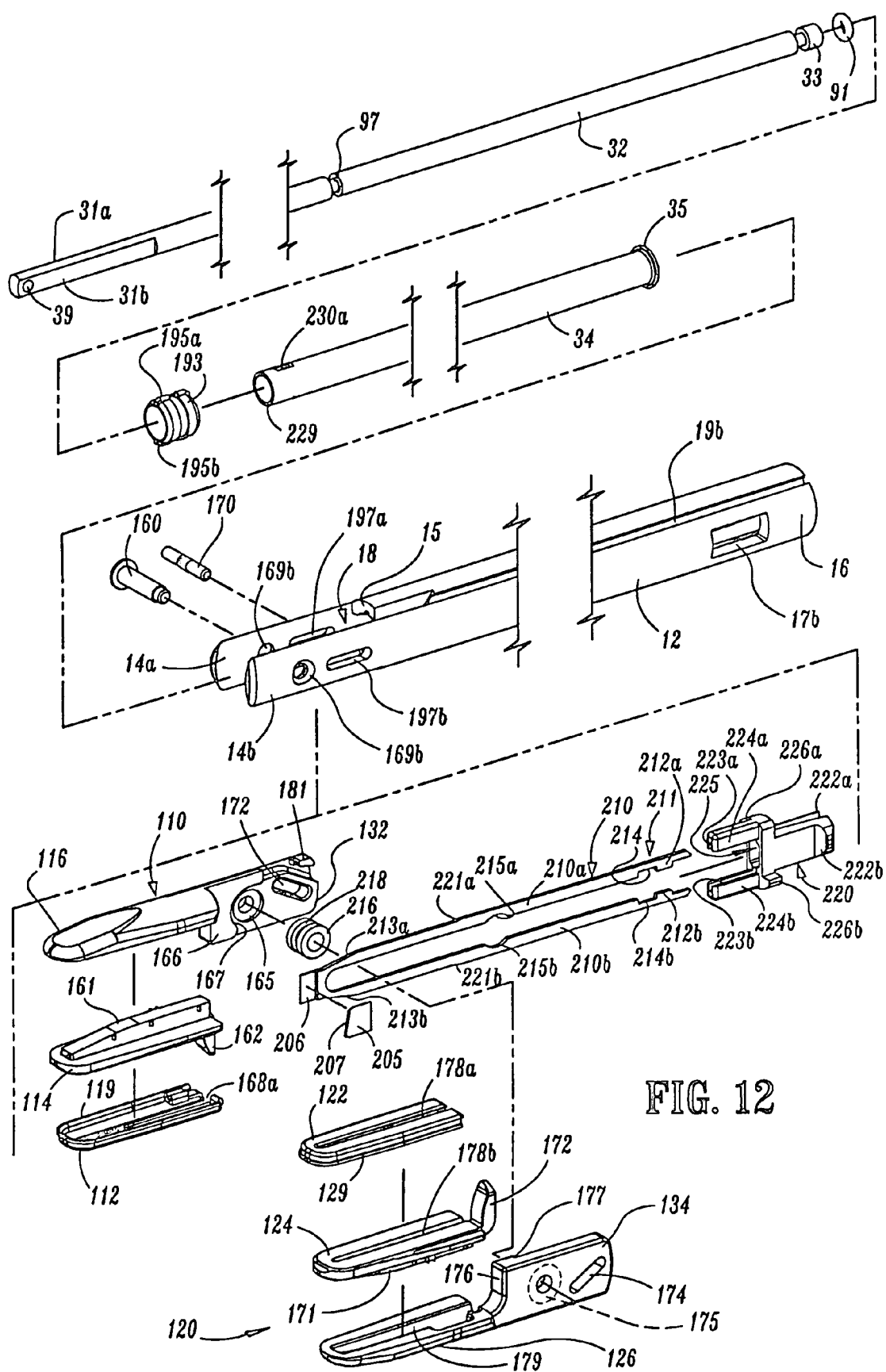
FIG. 12 is an exploded, perspective view of the end effector assembly, the knife assembly and the shaft.
Figure 13:
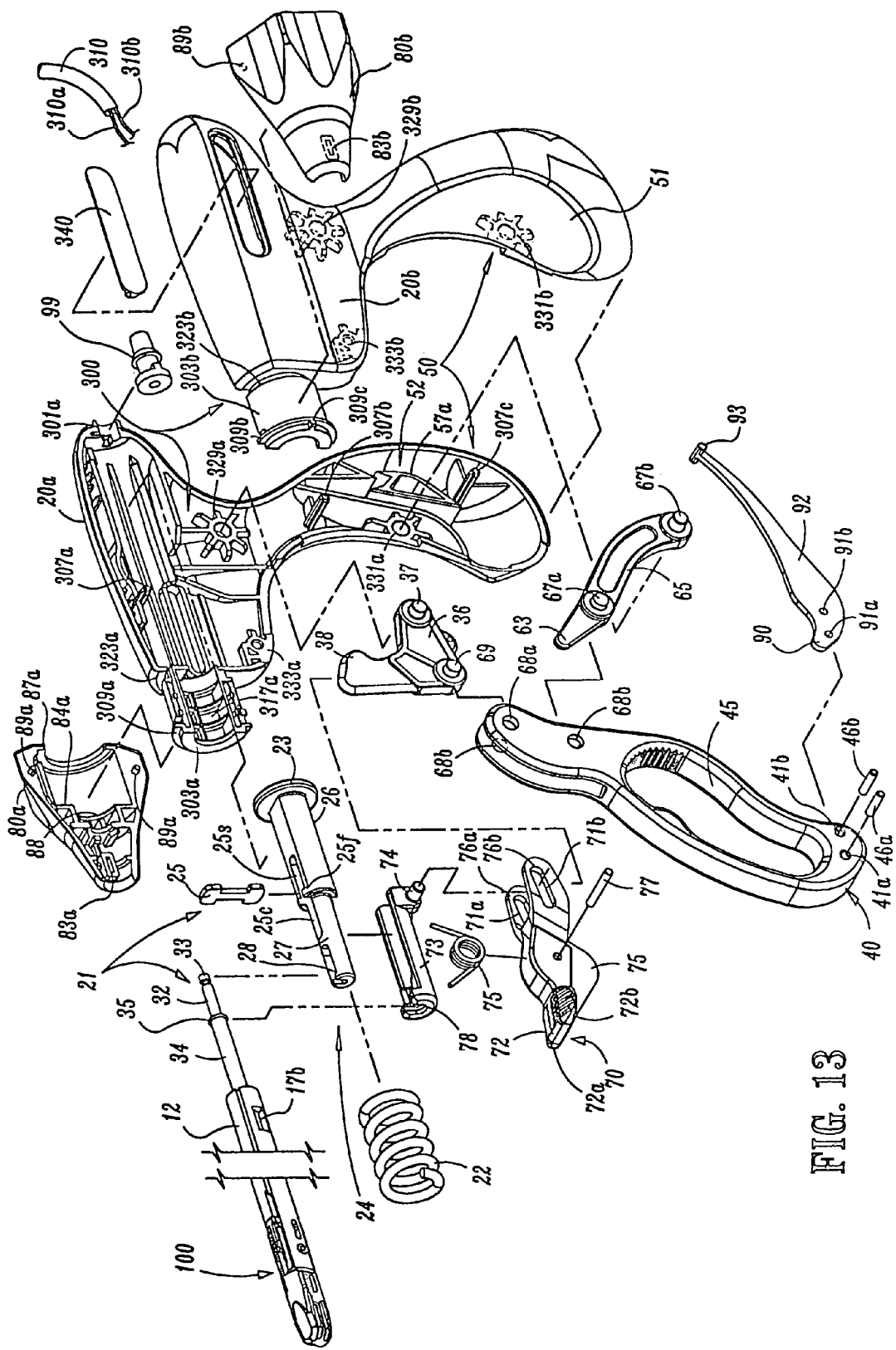
FIG. 13. is an exploded, perspective view of the housing and the internal working components thereof with the attachment of the shaft and end effector assembly to the housing shown in broken line illustration.

More particularly, forceps 10 includes a shaft 12 which has a distal end 14 dimensioned to mechanically engage the end effector assembly 100 and a proximal end 16 which mechanically engages the housing 20. Preferably, shaft 12 is bifurcated at the distal end 14 thereof to form ends 14a and 14b which are dimensioned to receive the end effector assembly 100 as best seen in FIGS. 7 and 12. The proximal end 16 of shaft 12 includes notches 17a (See FIGS. 23 and 29) and 17b (See FIGS. 11, 12 and 13) which are dimensioned to mechanically engage corresponding detents 83a (FIG. 18A) and 83b (FIG. 13 shown in phantom) of rotating assembly 80 as described in more detail below. In the drawings and in the descriptions which follow, the term "proximal", as is traditional, will refer to the end of the forceps 10 which is closer to the user, while the term "distal" will refer to the end which is further from the user.

Figure 1A:
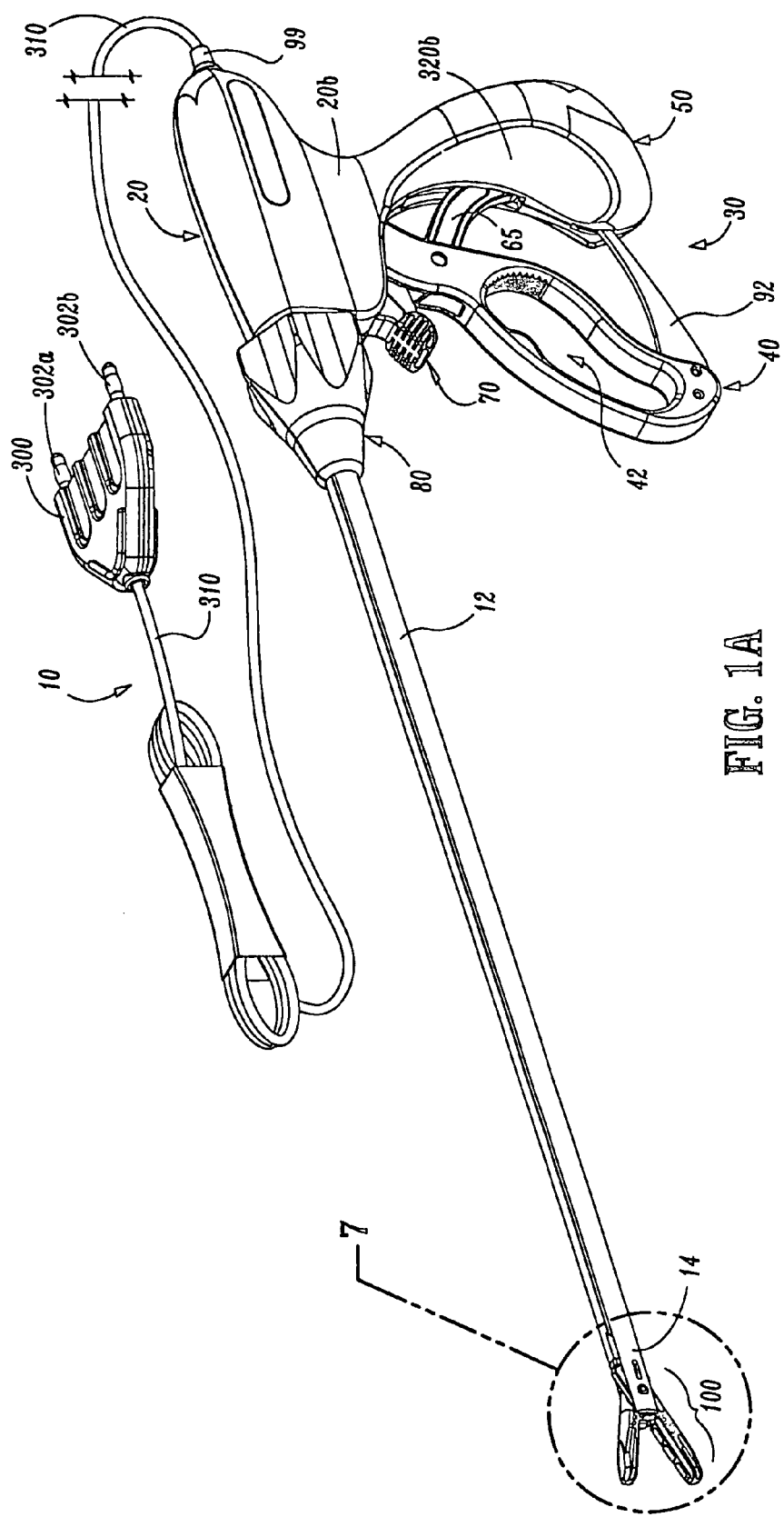
FIG. 1A is a left, perspective view of an endoscopic bipolar forceps showing a housing, a shaft and an end effector assembly according to the present disclosure.
Figure 1B:
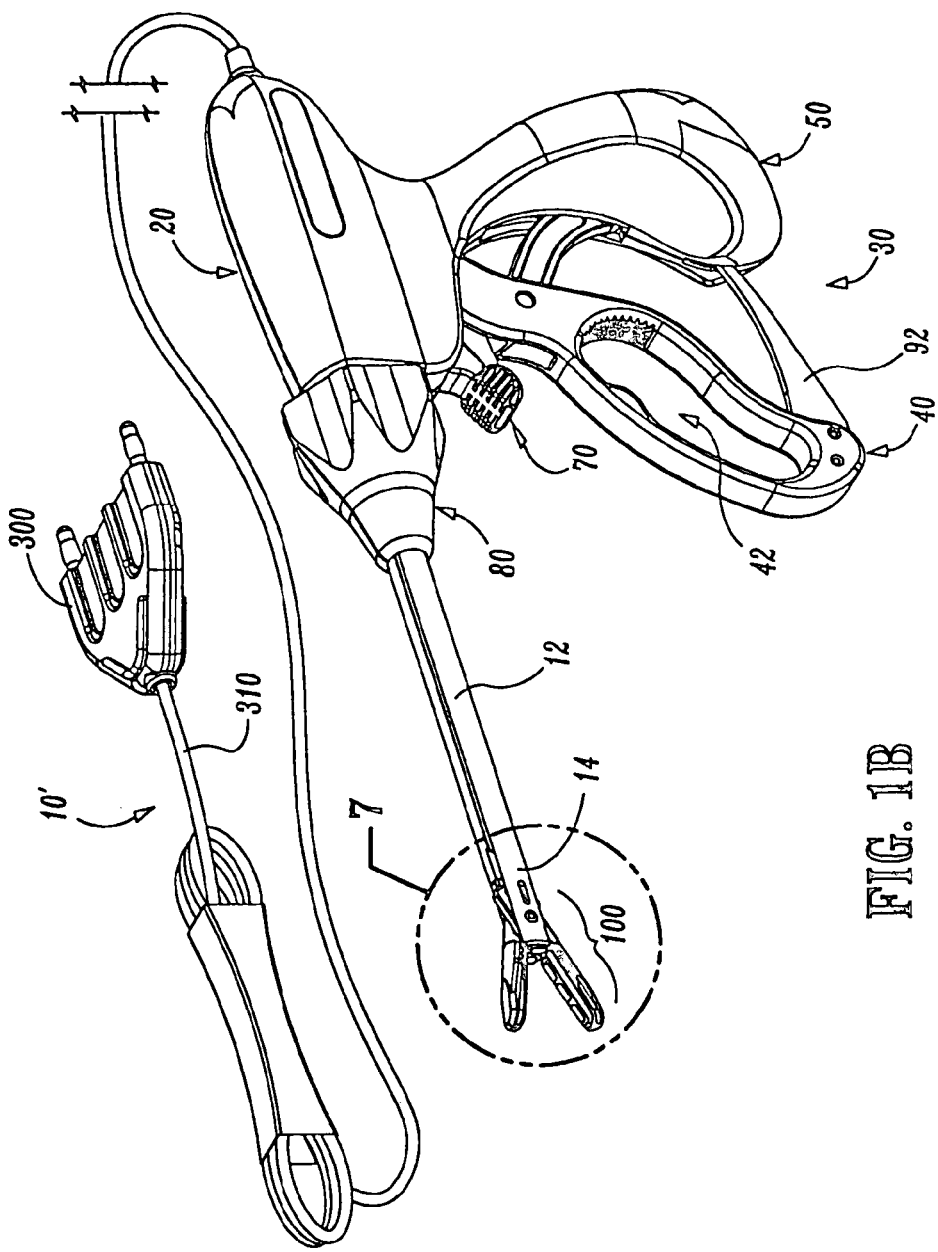
FIG. 1B is a left, perspective of an open bipolar forceps according to the present disclosure.
Figure 9:
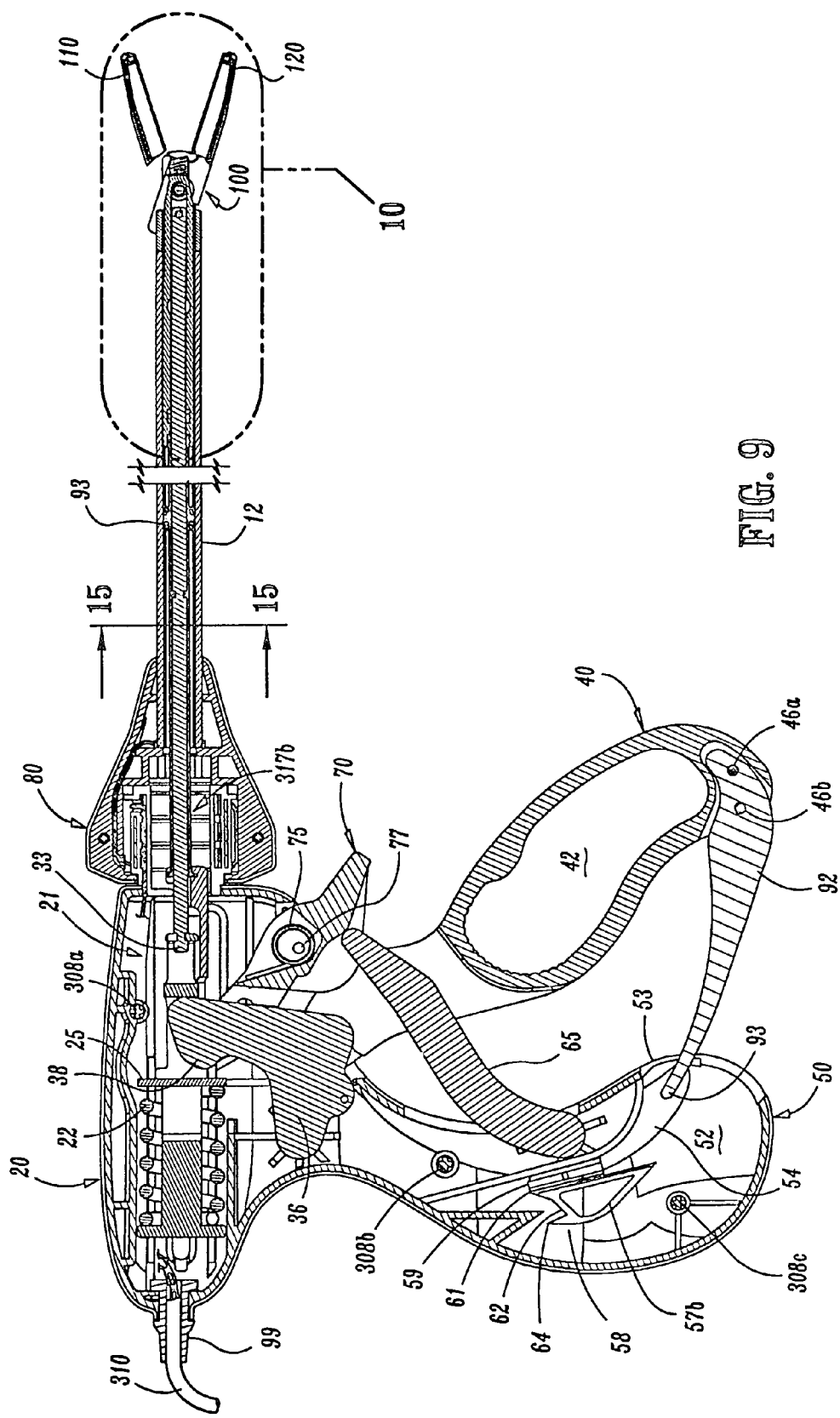
FIG. 9 is a slightly-enlarged, cross-section of the forceps of FIG. 3 showing the internal working components of the housing.
Figure 10:
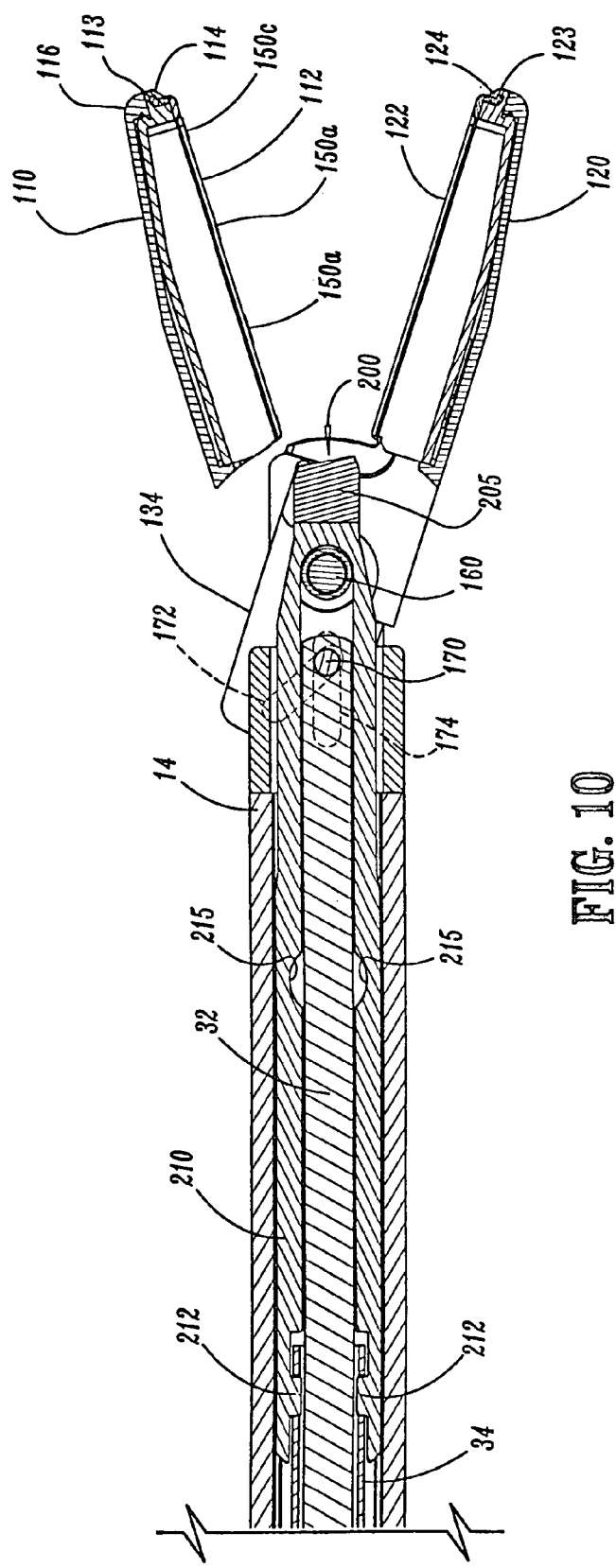
FIG. 10 is an enlarged, cross-section of the indicated area of detail of FIG. 9 showing the initial position of a knife assembly disposed within the end effector assembly.
Figure 18A:
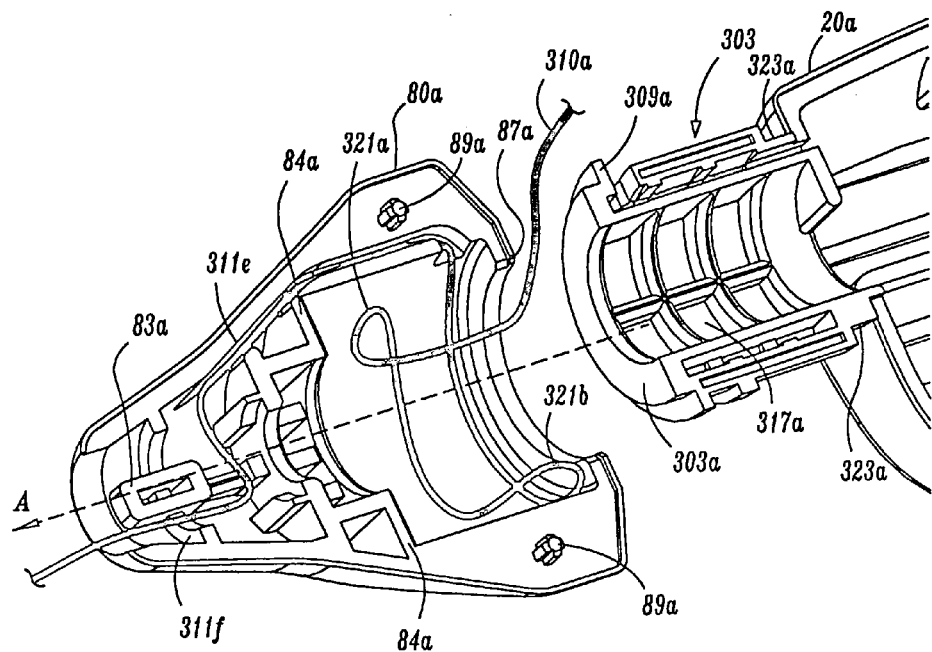
FIG. 18A is a greatly-enlarged, side perspective view of the housing without the cover plate showing the feed path for the electrical cable through a rotating assembly adjacent to a distal end of the housing.

As best seen in FIG. 1A, forceps 10 also includes an electrical interface or plug 300 which connects the forceps 10 to a source of electrosurgical energy, e.g., a generator (not shown). Plug 300 includes a pair of prong members 302a and 302b which are dimensioned to mechanically and electrically connect the forceps 10 to the source of electrosurgical energy. An electrical cable 310 extends from the plug 300 to a sleeve 99 which securely connects the cable 310 to the forceps 10. As best seen in FIGS. 9, 11 and 18A, cable 310 is internally divided into cable lead 310a and 310b which each transmit electrosurgical energy through their respective feed paths through the forceps 10 to the end effector assembly 100 as explained in more detail below.

Handle assembly 30 includes a fixed handle 50 and a movable handle 40. Fixed handle 50 is integrally associated with housing 20 and handle 40 is movable relative to fixed handle 50 as explained in more detail below with respect to the operation of the forceps 10. Rotating assembly 80 is preferably attached to a distal end 303 (FIG. 18A) of housing 20 and is rotatable approximately 180 degrees in either direction about a longitudinal axis "A".

Figure 2:
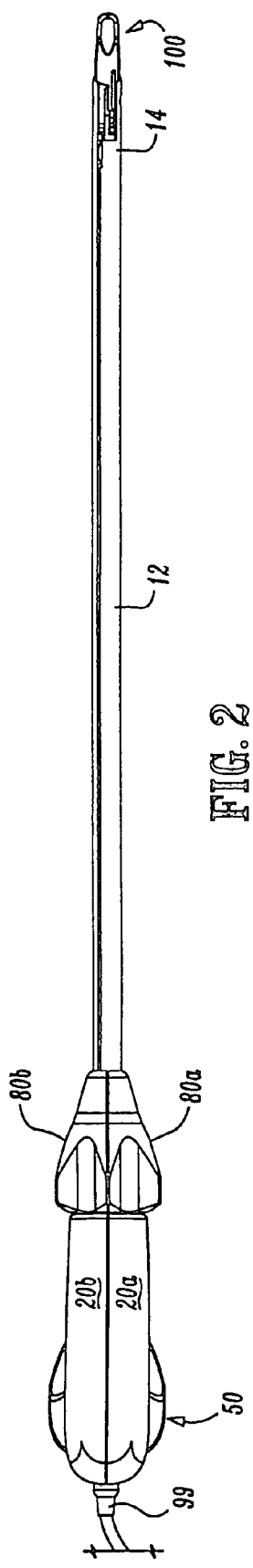
FIG. 2 is a top view of the forceps of FIG. 1.
Figure 3:
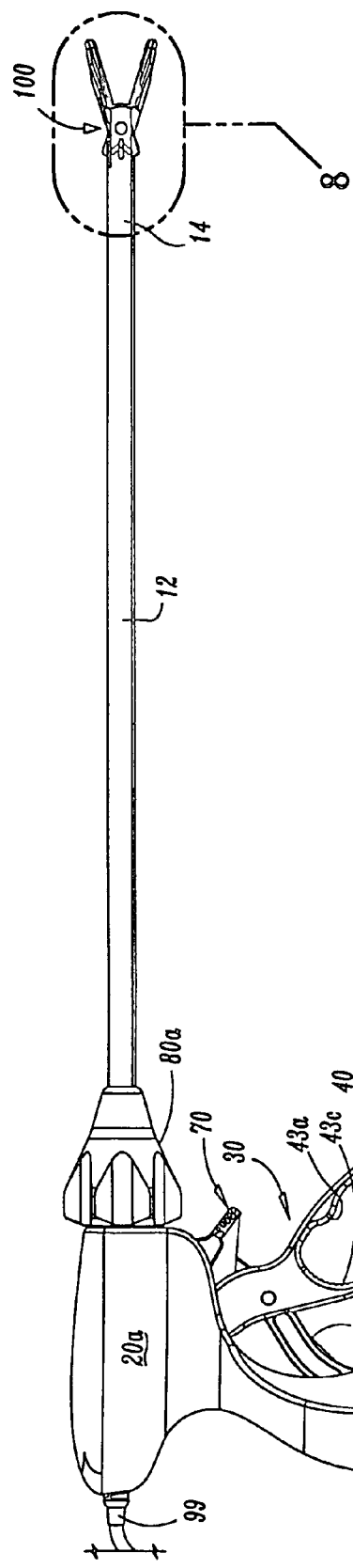
FIG. 3 is a right, side view of the forceps of FIG. 1.

As best seen in FIGS. 2 and 13, housing 20 is formed from two (2) housing halves 20a and 20b which each include a plurality of interfaces 307a, 307b and 307c (FIG. 13) which are dimensioned to mechanically align and engage one another to form housing 20 and enclose the internal working components of forceps 10. As can be appreciated, fixed handle 50 which, as mentioned above is integrally associated with housing 20, takes shape upon the assembly of the housing halves 20a and 20b.

It is envisioned that a plurality of additional interfaces (not shown) may disposed at various points around the periphery of housing halves 20a and 20b for ultrasonic welding purposes, e.g., energy direction/deflection points. It is also contemplated that housing halves 20a and 20b (as well as the other components described below) may be assembled together in any fashion known in the art. For example, alignment pins, snap-like interfaces, tongue and groove interfaces, locking tabs, adhesive ports, etc. may all be utilized either alone or in combination for assembly purposes.

Likewise, rotating assembly 80 includes two halves 80a and 80b which, when assembled, enclose and engage the proximal end 16 of shaft 12 to permit selective rotation of the end effector assembly 100 as needed. Half 80a includes a pair of detents 89a (FIG. 13) which are dimensioned to engage a pair of corresponding sockets 89b (shown in phantom in FIG. 13) disposed within half 80b. Movable handle 40 and trigger assembly 70 are preferably of unitary construction and are operatively connected to the housing 20 and the fixed handle 50 during the assembly process.

As mentioned above, end effector assembly 100 is attached to the distal end 14 of shaft 12 and includes a pair of opposing jaw members 110 and 120. Movable handle 40 of handle assembly 30 is ultimately connected to a drive rod 32 which, together, mechanically cooperate to impart movement of the jaw members 110 and 120 from an open position wherein the jaw members 110 and 120 are disposed in spaced relation relative to one another, to a clamping or closed position wherein the jaw members 110 and 120 cooperate to grasp tissue 420 (FIG. 20) therebetween. This is explained in more detail below with respect to FIGS. 9–11 and 20–29.

It is envisioned that the forceps 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of shaft 12 may be selectively and releasably engageable with the housing 20 and the handle assembly 30. In either of these two instances, the forceps 10 would be considered "partially disposable" or "reposable", i.e., a new or different end effector assembly 100 (or end effector assembly 100 and shaft 12) selectively replaces the old end effector assembly 100 as needed.

Turning now to the more detailed features of the present disclosure as described with respect to FIGS. 1A–13, movable handle 40 includes an aperture 42 defined therethrough which enables a user to grasp and move the handle 40 relative to the fixed handle 50. Handle 40 also includes an ergonomically-enhanced gripping element 45 disposed along the inner peripheral edge of aperture 42 which is designed to facilitate gripping of the movable handle 40 during activation. It is envisioned that gripping element 45 may include one or more protuberances, scallops and/or ribs 43a, 43b and 43c, respectively, to facilitate gripping of handle 40. As best seen in FIG. 11, movable handle 40 is selectively moveable about a pivot 69 from a first position relative to fixed handle 50 to a second position in closer proximity to the fixed handle 50 which, as explained below, imparts movement of the jaw members 110 and 120 relative to one another.

As shown best in FIG. 11, housing 20 encloses a drive assembly 21 which cooperates with the movable handle 40 to impart movement of the jaw members 110 and 120 from an open position wherein the jaw members 110 and 120 are disposed in spaced relation relative to one another, to a clamping or closed position wherein the jaw members 110 and 120 cooperate to grasp tissue therebetween. The handle assembly 30 can generally be characterized as a four-bar mechanical linkage composed of the following elements: movable handle 40, a link 65, a cam-like link 36 and a base link embodied by fixed handle 50 and a pair of pivot points 37 and 67b. Movement of the handle 40 activates the four-bar linkage which, in turn, actuates the drive assembly 21 for imparting movement of the opposing jaw members 110 and 120 relative to one another to grasp tissue therebetween. It is envisioned that employing a four-bar mechanical linkage will enable the user to gain a significant mechanical advantage when compressing the jaw members 110 and 120 against the tissue 420 as explained in further detail below with respect the operating parameters of the drive assembly 21. Although shown as a four-bar mechanical linkage, the present disclosure contemplates other linkages to effect relative motion of the jaw members 110 and 120 as is known in the art.

Preferably, fixed handle 50 includes an channel 54 defined therein which is dimensioned to receive a flange 92 which extends proximally from movable handle 40. Preferably, flange 92 includes a fixed end 90 which is affixed to movable handle 40 and a t-shaped free end 93 which is dimensioned for facile reception within channel 54 of handle 50. It is envisioned that flange 92 may be dimensioned to allow a user to selectively, progressively and/or incrementally move jaw members 110 and 120 relative to one another from the open to closed positions. For example, it is also contemplated that flange 92 may include a ratchet-like interface which lockingly engages the movable handle 40 and, therefore, jaw members 110 and 120 at selective, incremental positions relative to one another depending upon a particular purpose. Other mechanisms may also be employed to control and/or limit the movement of handle 40 relative to handle 50 (and jaw members 110 and 120) such as, e.g., hydraulic, semi-hydraulic, linear actuator(s), gas-assisted mechansims and/or gearing systems.

As best illustrated in FIG. 11, housing halves 20a and 20b of housing 20, when assembled, form an internal cavity 52 which predefines the channel 54 within fixed handle 50 such that an entrance pathway 53 and an exit pathway 58 are formed for reciprocation of the t-shaped flange end 93 therein. Once assembled, two generally triangular-shaped members 57a and 57b are positioned in close abutment relative to one another to define a rail or track 59 therebetween. During movement of the flange 92 along the entrance and exit pathways 53 and 58, respectively, the t-shaped end 93 rides along track 59 between the two triangular members 57a and 57b according to the particular dimensions of the triangularly-shaped members 57a and 57b, which, as can be appreciated, predetermines part of the overall pivoting motion of handle 40 relative to fixed handle 50.

Once actuated, handle 40 moves in a generally arcuate fashion towards fixed handle 50 about pivot 69 which causes link 65 to rotate proximally about pivots 67a and 67b which, in turn, cause cam-like link 36 to rotate about pivots 37 and 69 in a generally proximal direction. Movement of the cam-like link 36 imparts movement to the drive assembly 21 as explained in more detail below. Moreover, proximal rotation of the link 65 about pivots 67a and 67b also causes a distal end 63 of link 65 to release, i.e., "unlock", the trigger assembly 70 for selective actuation. This feature is explained in detail with reference to FIGS. 21–29 and the operation of the knife assembly 200.

Turning now to FIG. 12 which shows an the exploded view of the shaft 12 and end effector assembly 100. As mentioned above, shaft 12 includes distal and proximal ends 14 and 16, respectively. The distal end 14 is bifurcated and includes ends 14a and 14b which, together, define a cavity 18 for receiving the end effector assembly 100. The proximal end 16 includes a pair of notches 17a (FIG. 29) and 17b (FIG. 11) which are dimensioned to engage corresponding detents 83a and 83b (FIG. 13) of the rotating assembly 80. As can be appreciated, actuation of the rotation assembly 80 rotates the shaft 12 which, in turn, rotates the end effector assembly 100 to manipulate and grasp tissue 420.

Shaft 12 also includes a pair of longitudinally-oriented channels 19a (FIG. 15) and 19b (FIG. 12) which are each dimensioned to carry an electrosurgical cable lead 310a and 310b, respectively, therein for ultimate connection to each jaw member 120 and 110, respectively, as explained in more detail with reference to FIGS. 14–17 below. Shaft 12 also includes a pair of longitudinally oriented slots 197a and 197b disposed on ends 14a and 14b, respectively. Slots 197a and 197b are preferable dimensioned to allow longitudinal reciprocation of a cam pin 170 therein which, as explained below with reference to FIGS. 23 and 24, causes movement of the opposing jaw member 110 and 120 from the open to closed positions.

Shaft 12 also includes a pair of sockets 169a and 169b disposed at distal ends 14a and 14b which are dimensioned to receive a corresponding pivot pin 160. As explained below, pivot pin 160 secures jaws 110 and 120 to the shaft 12 between bifurcated distal ends 14a and 14b and mounts the jaw members 110 and 120 such that longitudinal reciprocation of the cam pin 170 rotates jaw members 110 and 120 about pivot pin 160 from the open to closed positions.

Figure 29:
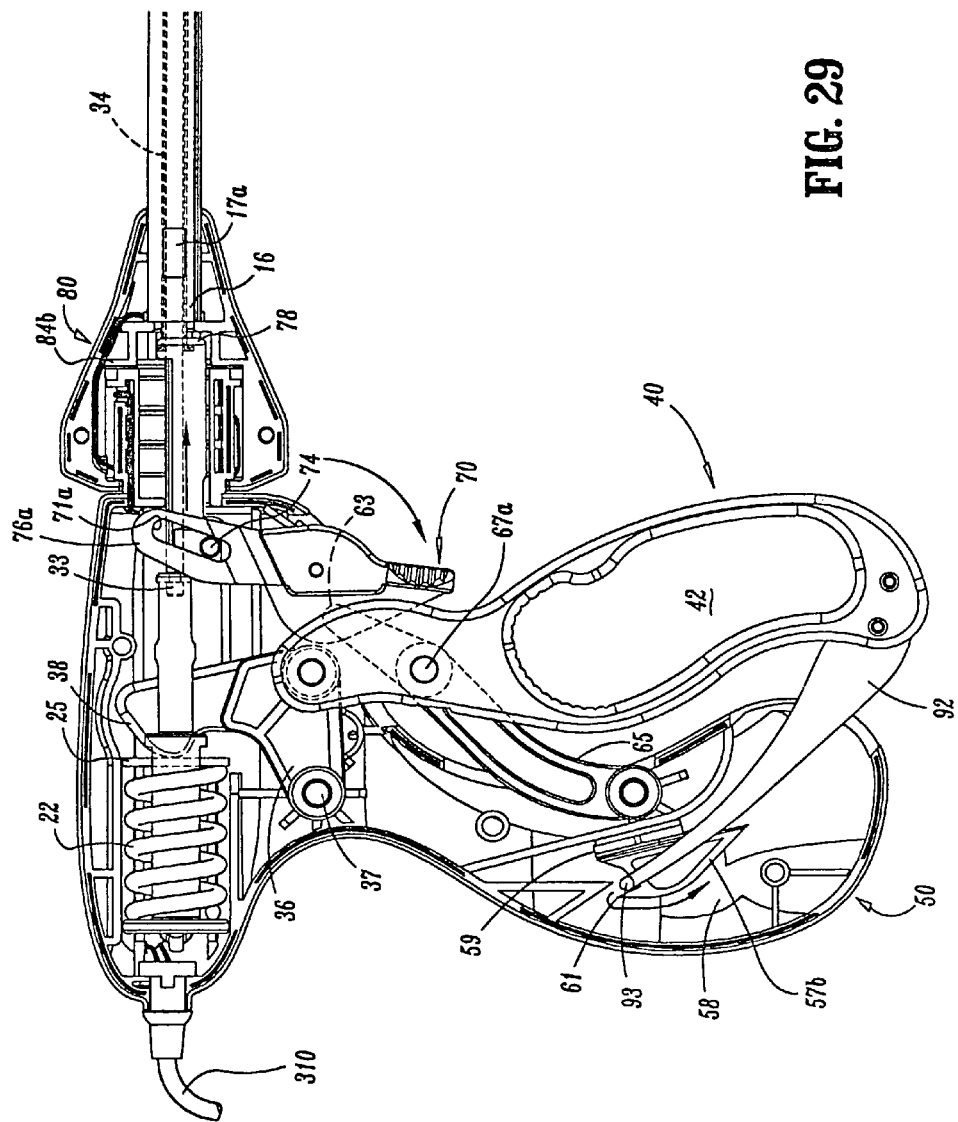
FIG. 29 is a side view of the housing without a cover plate showing the longitudinal reciprocation of the knife tube upon activation of a trigger assembly.

Shaft 12 is preferably dimensioned to slidingly receive a knife tube 34 therein which engages the knife assembly 200 such that longitudinal movement of the knife tube 34 actuates the knife assembly 200 to divide tissue 420 as explained below with respect to FIGS. 29–31. Knife tube 34 includes a rim 35 located at a proximal end thereof and a pair of opposing notches 230a and 230b (FIGS. 25 and 30) located at a distal end 229 thereof. As best shown in FIG. 13, rim 35 is dimensioned to engage a corresponding sleeve 78 disposed at a distal end of the trigger assembly 70 such that distal movement of the sleeve 78 translates the knife tube 34 which, in turn, actuates the knife assembly 200. A seal 193 may be mounted atop the knife tube 34 and positioned between the knife tube 34 and the shaft 12. It is envisioned that the seal 193 may be dimensioned to facilitate reciprocation of the knife tube 34 within the shaft 12 and/or to protect the other, more sensitive, internal operating components of the forceps from undesirable fluid inundation during surgery. Seal 193 may also be employed to control/regulate pneumo-peritoneal pressure leakage through forceps 10 during surgery. Seal 193 preferably includes a pair of opposing bushings 195a and 195b which assure consistent and accurate reciprocation of the knife tube 34 within shaft 12 (See FIG. 15).

Notches 230a and 230b are preferably dimensioned to engage a corresponding key-like interface 211 of the knife assembly 200 which includes a pair of opposing detents 212a and 212b and a pair of opposing steps 214a and 214b. As best illustrated in FIGS. 25 and 30, each detent and step arrangement, e.g., 212a and 214a, respectively, securely engages a corresponding notch, e.g., 230a, such that the distal end of the step 214a abuts the distal end 229 of the knife tube 34. It is envisioned that engaging the knife tube 34 to the knife assembly 200 in this manner will assure consistent and accurate distal translation of the knife tube 34 through the tissue 420.

As can be appreciated from the present disclosure, the knife tube 34 and knife assembly 200 are preferably assembled to operate independently from the operation of the drive assembly 21. However and as described in more detail below, knife assembly 200 is dependent on the drive assembly 21 for activation purposes, i.e., the activation/movement of the drive assembly 21 (via handle assembly 30 and the internal working components thereof) "unlocks" the knife assembly 200 for selective, separation of the tissue. For the purposes herein, the drive assembly 21 consists of both the drive rod 32 and the compression mechanism 24 which includes a number of cooperative elements which are described below with reference to FIG. 13. It is envisioned that arranging the drive assembly 21 in this fashion will enable facile, selective engagement of the drive rod 32 within the compression mechanism 24 for assembly purposes.

Although the drawings depict a disposable version of the presently disclosed forceps 10, it is contemplated that the housing 20 may include a release mechanism (not shown) which enables selectively replacement of the drive rod 32 for disposal purposes. In this fashion, the forceps will be considered "partially disposable" or "reposable", i.e., the shaft 12, end effector assembly 100 and knife assembly 200 are disposable and/or replaceable whereas the housing 20 and handle assembly 30 are re-usable.

As best illustrated in FIGS. 16 and 17, drive rod 32 includes a pair of chamfered or beveled edges 31a and 31b at a distal end thereof which are preferably dimensioned to allow facile reciprocation of the drive rod 32 through a knife carrier or guide 220 which forms a part of the knife assembly 200. A pin slot 39 is disposed at the distal tip of the drive rod 32 and is dimensioned to house the cam pin 170 such that longitudinal reciprocation of the drive rod 32 within the knife tube 34 translates the cam pin 170, which, in turn, rotates the jaw members 110 and 120 about pivot pin 160. As will be explained in more detail below with respect to FIGS. 23 and 24, the cam pin 170 rides within slots 172 and 174 of the jaw members 110 and 120, respectively, which causes the jaw members 110 and 120 to rotate from the open to closed positions about the tissue 420.

The proximal end of the drive rod 32 includes a tab 33 which is preferably dimensioned to engage a corresponding compression sleeve 28 disposed within the compression mechanism 24. Proximal movement of the sleeve 28 (as explained below with respect to FIGS. 21–24) reciprocates (i.e., pulls) the drive rod 32 which, in turn, pivots the jaw members 110 and 120 from the open to closed positions. Drive rod 32 also includes a donut-like spacer or o-ring 95 which is dimensioned to maintain pneumo-peritoneal pressure during endoscopic procedures. It is also envisioned that o-ring 95 may also prevent the inundation of surgical fluids which may prove detrimental to the internal operating components of the forceps 10. O-ring 95 is made also be made from a material having a low coefficient of friction to facilitate uniform and accurate reciprocation of the drive rod 32 within the knife tube 34.

As mentioned above, the knife assembly 200 is disposed between opposing jaw members 110 and 120 of the end effector assembly 100. Preferably, the knife assembly 200 and the end effector assembly 100 are independently operable, i.e., the trigger assembly 70 actuates the knife assembly 200 and the handle assembly 30 actuates the end effector assembly 100. Knife assembly 200 includes a bifurcated knife bar or rod 210 having two forks 210a and 210b and a knife carrier or guide 220. Knife forks 210a and 210b include the above-described key-like interfaces 211 (composed of steps 214a, 214b and detents 212a, 212b, respectively) disposed at the proximal end thereof for engaging the knife tube 34 (as described above) and a common distal end 206 which carries a blade 205 thereon for severing tissue 420. Preferably, each fork 210a and 210b includes a taper 213a and 213b, respectively, which converge to form common distal end 206. It is envisioned that the tapers 213a and 213b facilitate reciprocation of the knife blade 205 through the end effector assembly 100 as described in more detail below and as best illustrated in FIG. 30.

Each fork 210a and 210b also includes a tapered shoulder portion 221a and 221b disposed along the outer periphery thereof which is dimensioned to engage a corresponding slot 223a and 223b, respectively, disposed in the knife carrier or guide 220 (See FIG. 16). It is envisioned that this shoulder portion 221a, 221b and slot 223a, 223b arrangement may be designed to restrict and/or regulate the overall distal movement of the blade 205 after activation. Each fork 210a and 210b also includes an arcuately-shaped notch 215a and 215b, respectively disposed along the inward edge thereof which is dimensioned to facilitate insertion of a roller or bushing 216 disposed between the jaw members 110 and 120 during assembly.

As mentioned above, knife assembly 200 also includes a knife carrier or guide 220 which includes opposing spring tabs 222a and 222b at a proximal end thereof and upper and lower knife guides 224a and 224b, respectively, at the distal end thereof. The inner facing surface of each spring tab, e.g., 222b, is preferably dimensioned to matingly engage a corresponding chamfered edge, e.g., 31b of the drive rod 32 (FIG. 16) and the outer facing surface is preferably dimensioned for friction-fit engagement with the inner periphery of the shaft 12. As best seen in FIG. 12, knife carrier 220 also includes a drive rod channel 225 defined therethrough which is dimensioned to allow reciprocation of the drive rod 32 during the opening and closing of the jaw members 110 and 120. Knife guide 220 also includes rests 226a and 226b which extend laterally therefrom which abut the proximal ends 132, 134 of the jaw members 110 and 120 when disposed in the closed position.

Knife guides 224a and 224b preferably include slots 223a and 223b, respectively, located therein which guide the knife forks 210a and 210b therealong during activation to provide consistent and accurate reciprocation of the knife blade 205 through the tissue 420. It is envisioned that slots 223a and 223b also restrict undesirable lateral movements of the knife assembly 200 during activation. Preferably, the knife carrier 220 is positioned at a point slightly beyond the shoulder portions 221a and 221b when assembled.

The knife assembly 200 also includes a roller or bushing 216 which is dimensioned to mate with the inner peripheral edge of each fork 210a and 210b such that, during activation, the forks 210a and 210b glide over the roller or bushing 216 to assure facile and accurate reciprocation of the knife assembly 200 through the tissue 420. Bushing 216 is also dimensioned to seat between opposing jaw members 110 and 120 and is preferably secured therebetween by pivot pin 160. As mentioned above, the arcuately-shaped notches 215a and 215b facilitate insertion of the bushing 216 during assembly.

The end effector assembly 100 includes opposing jaw members 110 and 120 which are seated within cavity 18 defined between bifurcated ends 14a and 14b of shaft 12. Jaw members 110 and 120 are generally symmetrical and include similar component features which cooperate to permit facile rotation about pivot pin 160 to effect the sealing and dividing of tissue 420. As a result and unless otherwise noted, only jaw member 110 and the operative features associated therewith are describe in detail herein but as can be appreciated, many of these features apply to jaw member 120 as well.

More particularly, jaw member 110 includes a pivot flange 166 which has an arcuately-shaped inner surface 167 which is dimensioned to allow rotation of jaw member 110 about bushing 216 and pivot pin 160 upon reciprocation of drive rod 32 as described above. Pivot flange 166 also includes a cam slot 172 which is dimensioned to engage cam pin 170 such that longitudinal movement of the drive rod 32 causes the cam pin 170 to ride along cam slot 172. It is envisioned that cam slot 172 may be dimensioned to allow different rotational paths depending upon a particular purpose or to achieve a particular result. For example, commonly assigned, co-pending U.S. application Ser. No. 09/177,950 which is hereby incorporated by reference in its entirety herein, describes a two-stage cam slot arrangement which, as can be appreciated, provides a unique rotational path for the jaw members about the pivot point.

Pivot flange 166 also includes a recess 165 which is preferably dimensioned to secure one free end of the bushing 216 between jaw members 110 and 120. The inner periphery of recess 165 is preferably dimensioned to receive pivot pin 160 therethrough to secure the jaw member 110 to the shaft 12. Jaw member 120 includes a similar recess 175 (FIG. 14) which secures the opposite end of bushing 216 and jaw member 120 to shaft 12.

Jaw member 110 also includes a jaw housing 116, an insulative substrate or insulator 114 and an electrically conducive surface 112. Jaw housing 116 includes a groove (not shown—See groove 179 of jaw member 120) defined therein which is dimensioned to engage a ridge-like interface 161 disposed along the outer periphery of insulator 114. Insulator 114 is preferably dimensioned to securely engage the electrically conductive sealing surface 112. This may be accomplished by stamping, by overmolding, by overmolding a stamped electrically conductive sealing plate and/or by overmolding a metal injection molded seal plate. All of these manufacturing techniques produce an electrode having an electrically conductive surface 112 which is substantially surrounded by an insulating substrate 114. The insulator 114, electrically conductive sealing surface 112 and the outer, non-conductive jaw housing 116 are preferably dimensioned to limit and/or reduce many of the known undesirable effects related to tissue sealing, e.g., flashover, thermal spread and stray current dissipation.

Preferably, the electrically conductive sealing surface 112 may also include a pinch trim 119 (FIG. 25) which facilitates secure engagement of the electrically conductive surface 112 to the insulating substrate 114 and also simplifies the overall manufacturing process. It is envisioned that the electrically conductive sealing surface 112 may also include an outer peripheral edge which has a radius and the insulator 114 meets the electrically conductive sealing surface 112 along an adjoining edge which is generally tangential to the radius and/or meets along the radius. Preferably, at the interface, the electrically conductive surface 112 is raised relative to the insulator 114. These and other envisioned embodiments are discussed in concurrently-filed, co-pending, commonly assigned PCT application Ser. No. PCT/US01/11412 entitled "ELECTROSURGICAL INSTRUMENT WHICH REDUCES COLLATERAL DAMAGE TO ADJACENT TISSUE" by Johnson et al. and concurrently-filed, co-pending, commonly assigned PCT application Ser. No. PCT/US01/11411 entitled "ELECTROSURGICAL INSTRUMENT WHICH IS DESIGNED TO REDUCE THE INCIDENCE OF FLASHOVER" by Johnson et al. The entire contents of both of these applications are hereby incorporated by reference herein.

Figure 14:
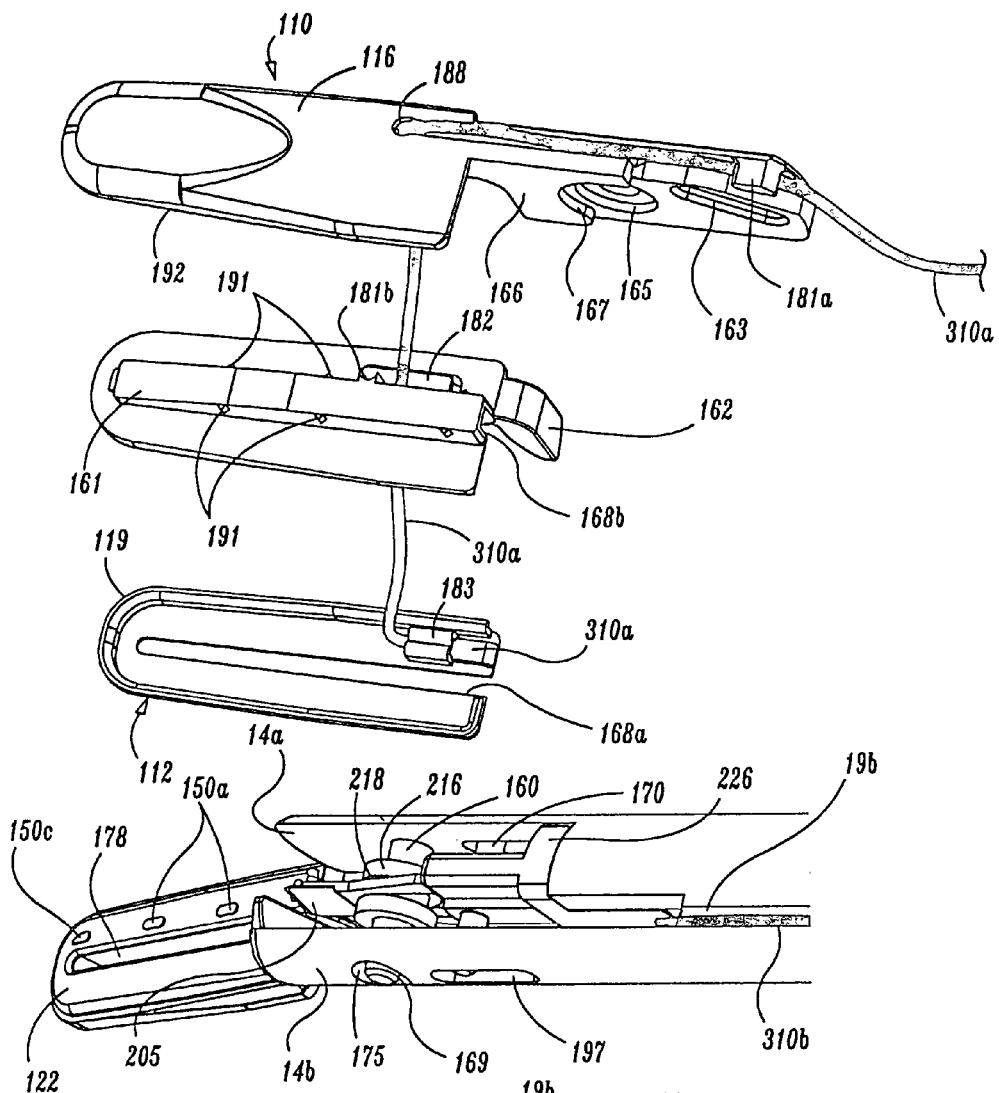
FIG. 14 is greatly-enlarged, top perspective view of the end effector assembly with parts separated showing a feed path for an electrical cable through the top jaw member.

Insulator 114 also includes an inwardly facing finger 162 which abuts pivot flange 166 and is designed to restrict/reduce proximal tissue spread and/or isolate the electrically conductive sealing surface 112 from the remaining end effector assembly 100 during activation. Preferably, the electrically conductive surface 112 and the insulator 114, when assembled, form a longitudinally-oriented channel 168a, 168b defined therethrough for reciprocation of the knife blade 205. More particularly, and as best illustrated in FIG. 14, insulator 114 includes a first channel 168b which aligns with a second channel 168a on electrically conductive sealing surface 112 to form the complete knife channel. It is envisioned that the knife channel 168a, 168b facilitates longitudinal reciprocation of the knife blade 205 along a preferred cutting plane "B—B" to effectively and accurately separate the tissue 420 along the formed tissue seal 425 (See FIGS. 27, 28 and 31.

As mentioned above, jaw member 120 include similar elements which include: a pivot flange 176 which has an arcuately-shaped inner surface 177, a cam slot 174, and a recess 175; a jaw housing 126 which includes a groove 179 which is dimensioned to engage a ridge-like interface 171 disposed along the outer periphery of an insulator 124; the insulator 124 which includes an inwardly facing finger 172 which abuts pivot flange 176; and an electrically conducive sealing surface 122 which is dimensioned to securely engage the insulator 124. Likewise, the electrically conductive surface 122 and the insulator 124, when assembled, form a longitudinally-oriented channel 178a, 178b defined therethrough for reciprocation of the knife blade 205.

Figure 15:
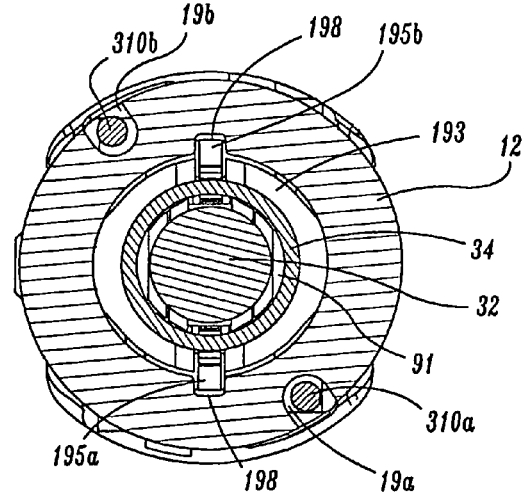
FIG. 15 is a longitudinal, cross-section of the indicated area of detail of FIG. 9.

Preferably, the jaw members 110 and 120 are electrically isolated from one another such that electrosurgical energy can be effectively transferred through the tissue 420 to form seal 425. For example and as best illustrated in FIGS. 14 and 15, each jaw member, e.g., 110, includes a uniquely-designed electrosurgical cable path disposed therethrough which transmits electrosurgical energy to the electrically conductive sealing surfaces 112, 122. More particularly, jaw member 110 includes a cable guide 181a disposed atop pivot flange 166 which directs cable lead 310a towards an aperture 188 disposed through jaw housing 116. Aperture 188, in turn, directs cable lead 310a towards electrically conductive sealing surface 112 through a window 182 disposed within insulator 114. A second cable guide 181b secures cable lead 310a along the predefined cable path through window 182 and directs a terminal end 310a' of the cable lead 310a into crimp-like electrical connector 183 disposed on an opposite side of the electrically conductive sealing surface 112. Preferably, cable lead 310a is held loosely but securely along the cable path to permit rotation of the jaw member 110 about pivot 169.

As can be appreciated, this isolates electrically conductive sealing surface 112 from the remaining operative components of the end effector assembly 100 and shaft 12. Jaw member 120 includes a similar cable path disposed therein and therethrough which includes similarly dimensioned cable guides, apertures and electrical connectors which are not shown in the accompanying illustrations.

FIGS. 15–17 also show the presently disclosed feed path for both electrosurgical cable leads 310a and 310b along the outer periphery of the shaft 12 and through each jaw member 110 and 120. More particularly, FIG. 15 shows a cross section of the electrosurgical cable leads 310a and 310b disposed within channels 19a and 19b, respectively, along shaft 12. FIGS. 16 and 17 show the feed path of the cable leads 310a and 310b from the opposite channels 19a and 19b of the shaft 12 through the pivot flanges 166 and 176 of the jaw members 110 and 120, respectively. It is contemplated that this unique cable feed path for cable leads 310a and 310b from the shaft 12 to the jaw members 110 and 120 not only electrically isolates each-jaw member 100 and 120 but also allows the jaw members 110 and 120 to pivot about pivot pin 160 without unduly straining or possibly tangling the cable leads 310a and 310b. Moreover, it is envisioned that the crimp-like electrical connector 183 (and the corresponding connector in jaw member 120) greatly facilitates the manufacturing and assembly process and assures a consistent and tight electrical connection for the transfer of energy through the tissue 420. As best shown in FIG. 17, the outer surface of shaft 12 may be covered by heat shrink tubing 500 or the like which protects the cable leads 310a and 310b from undue wear and tear and secures cable leads 310a and 310b within their respective channels 19a and 19b.

Figure 18B:
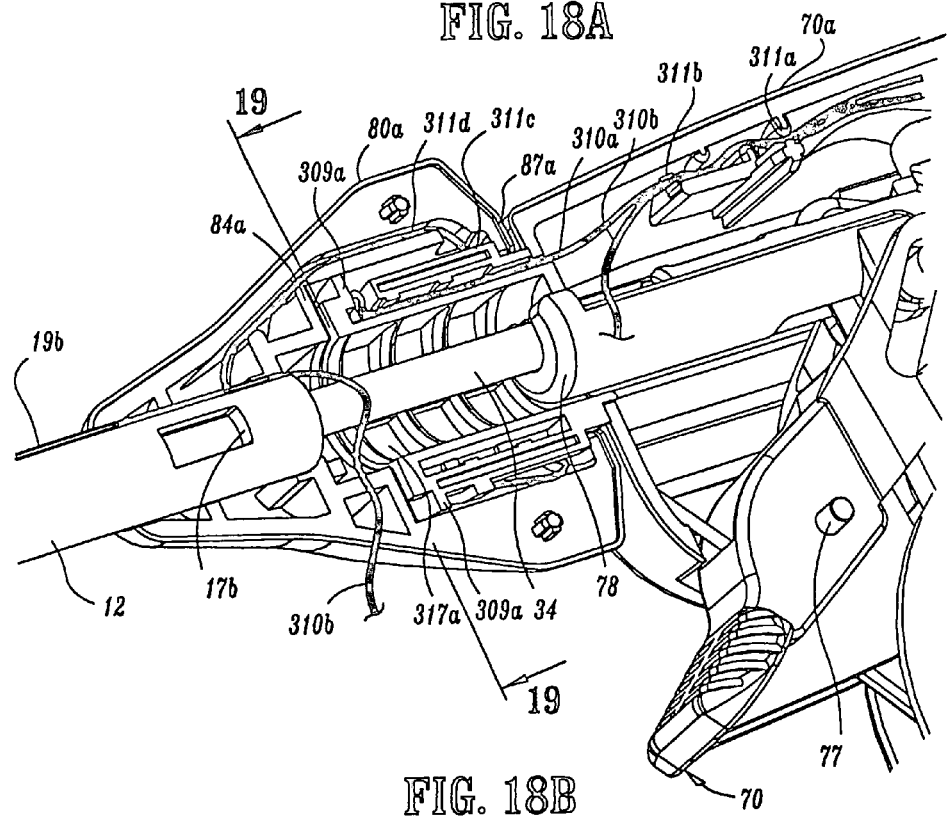
FIG. 18B is a greatly-enlarged, side perspective view of the housing without the cover plate showing the feed path for the electrical cable through a rotating assembly with the shaft mounted within the housing.

FIGS. 18A and 18B show the feed path of the cable leads 310a and 310b through the rotating assembly 80 which, again, allows the user added flexibility during the use of the forceps 10 due to the uniqueness of the feed path. More particularly, FIG. 18A shows the feed path of cable lead 310a through half 80a of the rotating assembly 80 and FIG. 18B shows the path of cable leads 310a and 310b as the cable leads 310a and 310b feed through the instrument housing 20a, through half 80a of the rotating assembly 80 and to the channels 19a and 19b of the shaft 12. FIG. 18A only shows the feed path of cable lead 310a through half 80a of the rotating assembly 80, however, as can be appreciated, cable lead 310b (shown broken in FIG. 19) is positioned in a similar fashion within half 80b of rotating assembly 80.

As best illustrated in FIG. 18A, it is envisioned that cable leads 310a and 310b are fed through respective halves 80a and 80b of the rotating assembly 80 in such a manner to allow rotation of the shaft 12 (via rotation of the rotating assembly 80) in the clockwise or counter-clockwise direction without unduly tangling or twisting the cable leads 310a and 310b. More particularly, each cable lead, e.g., 310a, is looped through each half 80a of the rotating assembly 80 to form slack-loops 321a and 321b which traverse either side of longitudinal axis "A". Slack-loop 321a redirects cable lead 310a across one side of axis "A" and slack-loop 321b returns cable lead 310a across axis "A". It is envisioned that feeding the cable leads 310a and 310b through the rotating assembly 80 in this fashion allows the user to rotate the shaft 12 and the end effector assembly 100 without unduly straining or tangling the cable leads 310a and 310b which may prove detrimental to effective sealing. Preferably, this loop-like cable feed path allows the user to rotate the end effector assembly 100 about 180 degrees in either direction without straining the cable leads 310a and 310b. The presently disclosed cable lead feed path is envisioned to rotate the cable leads 310a and 310b approximately 178 degrees in either direction.

Figure 19:
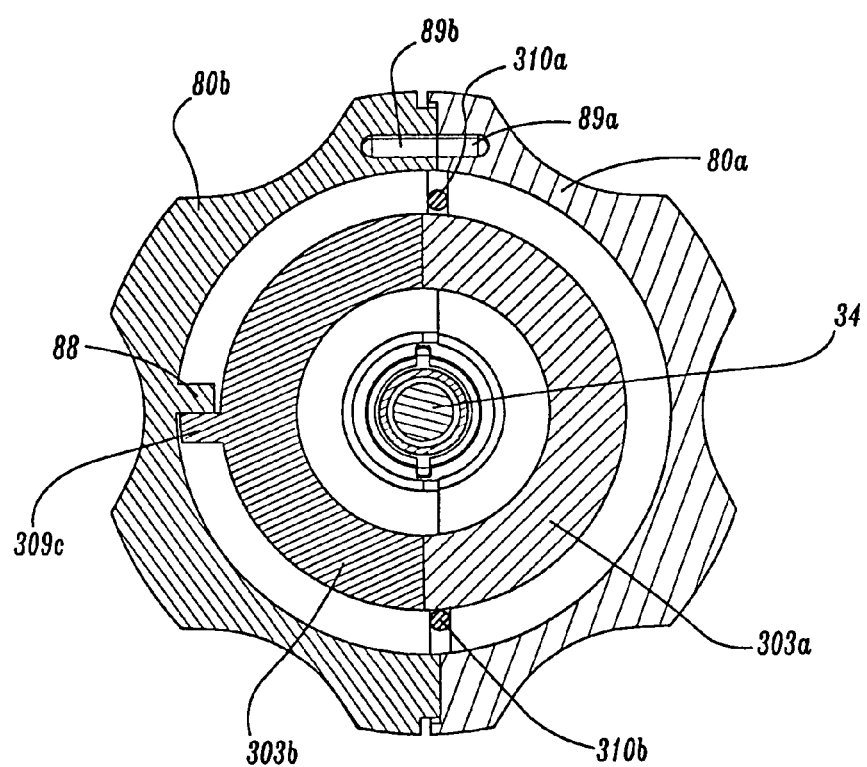
FIG. 19 is a greatly-enlarged, rear view of the rotating assembly showing an internally-disposed stop member.

FIG. 19 shows an internal view of half 80a of the rotating assembly 80 as viewed along axis "A" to highlight the internal features thereof. More particularly, at least one stop 88 is preferably positioned within each rotating half 80a and 80b which operates to control the overall rotational movement of the rotating assembly 80 to about 180 degree in either direction. The stop member 88 is dimensioned to interface with a corresponding notch 309c disposed along the periphery of outer flange 309 to prevent unintended over-rotation of the rotating assembly 80 which may unduly strain one or both of the cable leads 310a and 310b.

FIG. 18B shows the feed path of the electrical cable leads 310a and 310b from the housing 20a, through the rotating assembly 80 and to the shaft 12. It is envisioned that the cable leads 310a and 310b are directed through each part of the forceps 10 via a series of cable guide members 311a–311b disposed at various positions through the housing 20 and rotating assembly 80. As explained below, a series of mechanical interfaces, e.g., 309a, 309b (FIG. 13) and 323a, 323b (FIG. 13) may also be dimensioned to contribute in guiding cables 310a and 310b through the housing 20 and rotating assembly 80.

Turning back to FIG. 13 which shows the exploded view of the housing 20, rotating assembly 80, trigger assembly 70 and handle assembly 30, it is envisioned that all of these various component parts along with the shaft 12 and the end effector assembly 100 are assembled during the manufacturing process to form a partially and/or fully disposable forceps 10. For example and as mentioned above, the shaft 12 and/or end effector assembly 100 may be disposable and, therefore, selectively/releasably engagable with the housing 20 and rotating assembly 80 to form a partially disposable forceps 10 and/or the entire forceps 10 may be disposable after use.

Housing 20 is preferably formed from two housing halves 20a and 20b which engage one another via a series of mechanical interfaces 307a, 307b, 307c and 308a, 308b, 308c respectively, to form an internal cavity 300 for housing the hereindescribed internal working components of the forceps 10. For the purposes herein, housing halves 20a and 20 are generally symmetrical and, unless otherwise noted, a component described with respect to housing half 20a will have a similar component which forms a part of housing half 20b.

Figures 21, 22:
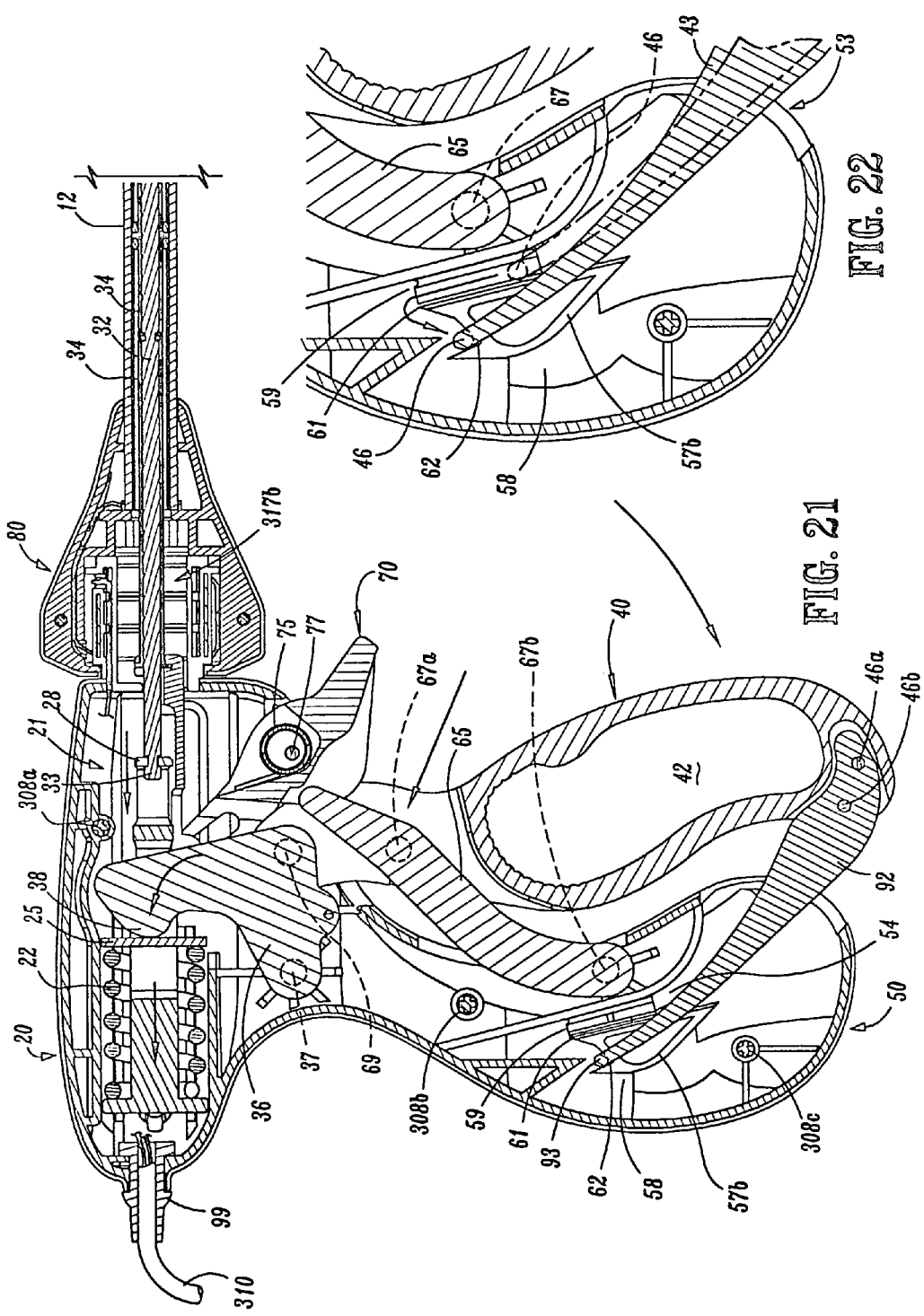
FIG. 21 is a slightly-enlarged, cross-section of the internal, cooperative movements of a four-bar handle assembly disposed within the housing which effects movement of the jaw members relative to one another.
FIG. 22 is a greatly-enlarged, cross-section showing the initial movement of a flange upon activation of the four-bar handle assembly shown in phantom illustration.

Housing half 20a includes proximal and distal ends 301a and 303a, respectively. Proximal end 301a is preferably dimensioned to receive an electrical sleeve 99 which secures the electrosurgical cable. 310 (FIG. 1) within the housing 20. As best shown in FIGS. 9 and 21, paired cable 310 splits into two electrosurgical cable leads 310a and 310b which are subsequently fed through the housing 20 to ultimately transmit different electrical potentials to the opposing jaw members 110 and 120. As mentioned above, various cable guides 311a–311g are positioned throughout the housing 20 and the rotating assembly 80 to direct the cable leads 310a and 310b to the channels 19a and 19b disposed along the outer periphery of the shaft 12.

The distal end 303a is generally arcuate in shape such that, when assembled, distal ends 303a and 303b form a collar 303 (FIG. 13) which extends distally from the housing 20. Each distal end 303a, 303b of the collar 303 includes an outer flange 309a, 309b and a recess 323a, 323b which cooperate to engage corresponding mechanical shoulders 84a, 84b (FIG. 29) and flanges 87a, 87b, respectively, disposed within the rotating assembly 80. As can be appreciated, the interlocking engagement of the flanges 309a, 309b with the shoulders 84a, 84b and the recesses 323a, 323b with the flanges 87a, 87b are dimensioned to allow free rotation about of the rotating assembly 80 about collar 303 when assembled. As mentioned above, the stop member(s) 88 and the notch(es) mechanically cooperate to limit rotational movement of the rotating assembly 80 to avoid straining cable leads 310a and 310b.

Each distal end 303a, 303b of collar 303 also includes an inner cavity 317a and 317b (FIGS. 9 and 21), respectively, defined therein which is dimensioned to permit free rotation of the shaft 12, knife tube 34 and cable leads 310a and 310b housed therein. A plurality of detents 89a located within rotating assembly 80 engage a corresponding plurality of sockets 89b (FIG. 13) disposed within rotating half 80b to poise the rotating assembly 80 in rotational relationship atop collar 303.

Housing half 20a also includes a plurality of hub-like pivot mounts 329a, 331a and 333a which as explained in more detail below with respect to the operation of the instrument, cooperate with opposite hub-like pivot mounts (shown in phantom in FIG. 13) disposed on housing half 20b to engage the free ends of pivot pins 37, 67b and 77, respectively, which are associated with the different operating components described below. Preferably, each of these mounts 329a, 331a and 333a provide a fixed point of rotation for each pivoting element, namely, cam link 36, handle link 65 and trigger assembly 70, respectively.

As best seen in FIGS. 11 and 13, fixed handle 50 which takes shape upon the assembly of housing 20 includes a scallop-like outer surface 51 and an internal cavity 52 defined therein. As mentioned above with respect to the discussion of FIG. 11, these elements and the other internal elements of the fixed handle 50 cooperate with movable handle 40 to activates the four-bar mechanical linkage which, in turn, actuates the drive assembly 21 for imparting movement of the opposing jaw members 110 and 120 relative to one another to grasp tissue 420 therebetween.

The handle assembly 30 which includes the above-mentioned fixed handle 50 and movable handle 40 also includes the cam link 36 which is generally triangular in shape. The cam link includes an upper piston 38, a fixed pivot 37 and a handle pivot 69. Cam link is assembled within the internal cavity 300 of housing 20 between housing halves 20a and 20b. More particularly, fixed pivot 37 is rotatingly mounted within fixed mounts 329a and 329b between opposing housing halves 20a and 20b and the handle pivot 69 is rotatingly mounted within the bifurcated end of handle 40 through apertures 68a and 68b. Cam piston 38 is poised within a longitudinal channel 25c defined through the drive assembly 70 (explained in further detail below with respect to the discussion of the drive assembly 70) in abutting relationship with a compression tab 25 such that movement of the handle 40 rotates piston 38 proximally against coil spring 22. These and the other details relating to the operational features are discussed below with reference to FIGS. 21–29.

Link 65 is also associated with the handle assembly 30 and forms an integral part of the four-bar mechanical linkage. Link 65 includes a distal end 63 and two pivot pins 67a and 67b. Pivot pin 67a engages apertures 68a and 68b disposed within the movable handle 40 and pivot 67b engages fixed mounts 331a and 331b between housing halves 20a and 20b such that movement of the handle 40 towards fixed handle 50 pivots link 65 about pivots 67a and 67b. As explained in more detail below, distal end 63 acts as a lockout for the trigger assembly 70.

Movable handle 40 includes a flange 92 which is preferably mounted to the movable handle 40 by pins 46a and 46b which engage apertures 41a and 41b disposed within handle 40 and apertures 91a and 91b disposed within flange 92, respectively. Other methods of engagement are also contemplated, snap-lock, spring tab, etc. Flange 92 also includes a t-shaped distal end 93 which, as mentioned above with respect to FIG. 11, rides within a predefined channel 54 disposed within fixed handle 50. Additional features with respect to the t-shaped end 93 are explained below in the detailed discussion of the operational features of the forceps 10.

A drive assembly 21 is preferably positioned within the housing 20 between housing halves 20a and 20b. As discussed above, the drive assembly 21 includes the previously described drive rod 32 and the compression mechanism 24. Compression mechanism 24 includes a compression sleeve 27 which is telescopically and/or slidingly disposed within a spring mount 26. The distal end 28 of the compression sleeve 27 is preferably C-shaped and dimensioned to engage the tab 33 disposed at the proximal end of drive rod 32 such that longitudinal movement of the compression sleeve 27 actuates the drive rod 32. The proximal end of the compression sleeve 27 is dimensioned to engage a barbell-shaped compression tab 25 which is disposed within a longitudinal slot 25s of the spring mount 26. The compression sleeve 27 also includes a longitudinal slot or channel 25c which is longitudinally aligned with slot 25s and is dimensioned to receive the cam piston 38 of the cam link 36 described above.

The proximal end of spring mount 26 includes a circular flange 23 which is dimensioned to bias the compression spring 22 once the compression mechanism 24 is assembled and seated within housing 20 (FIG. 11). The distal end of spring mount 26 includes a flange 25f which restricts distal movement of the tab 25 to within the slot 25s of the spring mount 26 and biases the opposite end the spring 22.

As best seen in FIG. 11, once assembled, spring 22 is poised for compression atop spring mount 26 upon actuation of the handle assembly 30. More particularly, movement of the cam piston 38 within slot 25c (via movement of handle assembly 30) moves the tab 25 atop slot 25s and reciprocates the compression sleeve 27 within the spring mount 26 to compress the spring 22. Proximal movement of the compression sleeve 27 imparts proximal movement to the drive rod 32 which closes jaw members 110 and 120 about tissue 420 (FIG. 26). Compression of the spring 22 may be viewed through one or more windows 340 disposed within the housing halves, e.g., 20b.

FIG. 13 also shows the trigger assembly 70 which activates the knife assembly 200 as described above with respect to FIG. 12. More particularly, trigger assembly 70 includes an actuator 73 having a cuff-like distal end 78 which is dimensioned to receive the proximal rim 35 of the knife tube 34. A drive pin 74 extends laterally from the proximal end of actuator 73. Trigger assembly 70 also includes an ergonomically enhanced finger tab 72 having opposing wing-like flanges 72a and 72b which are envisioned to facilitate gripping and firing of the trigger assembly during surgery.

As best shown in FIG. 11, the compression sleeve 27 is dimensioned to slide internally within actuator 73 when the forceps 10 is assembled. Likewise, the actuator 73, when activated, can slide distally along the outer periphery of compression sleeve 27 to actuate the knife assembly 200 as described above with respect to FIG. 12. The drive pin 74 is dimensioned to ride along a pair of guide rails 71a and 71b disposed within a bifurcated tail portion of finger tab 72 which includes ends 76a and 76b, respectively.

Figure 27:
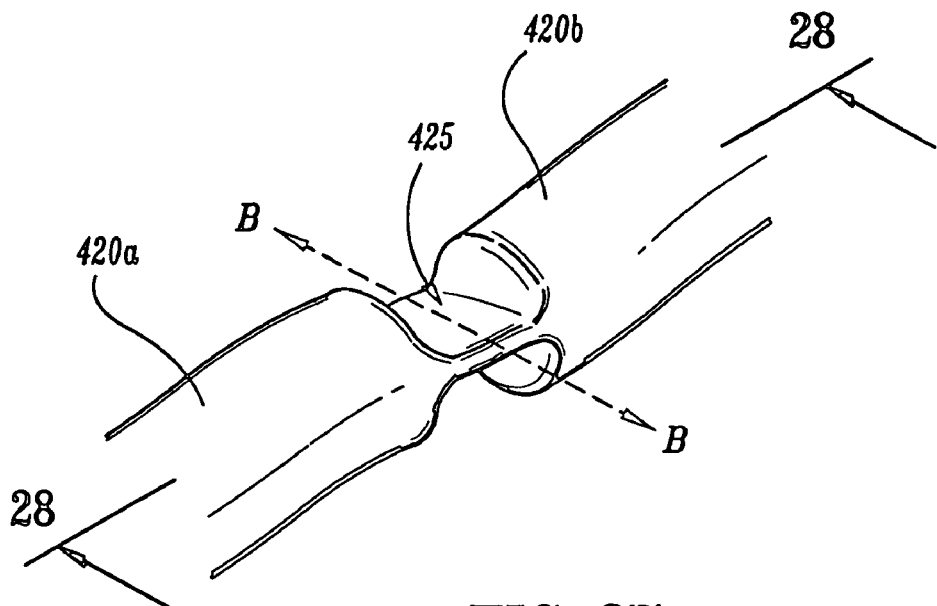
FIG. 27 is an enlarged perspective view of a seaed site of a tubular vessel showing a preferred cutting line "B—B" for dividing the tubular vessel after sealing.
Figure 28:
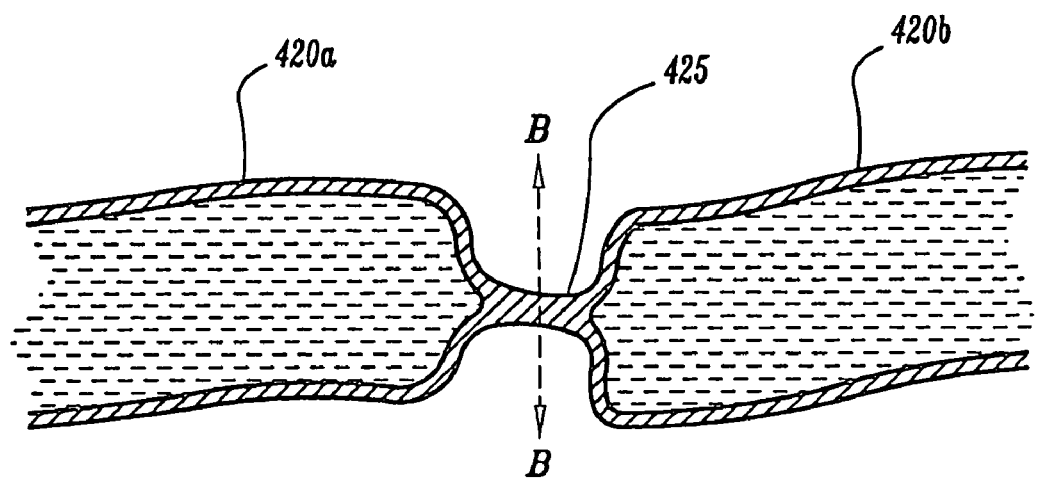
FIG. 28 is a longitudinal cross-section of the sealed site taken along line 28—28 of FIG. 27.

A hinge or pivot pin 77 mounts the finger tab 72 between housing halves 20a and 20 within mounts 333a and 333b. A torsion spring 75 may also be incorporated within the trigger assembly 70 to facilitate progressive and consistent longitudinal reciprocation of the actuator 73 and knife tube 34 to assure reliable separation along the tissue seal 425 (FIGS. 27 and 28). In other words, the trigger assembly 70 is configured in a proximal, "pre-loaded" configuration prior to activation. This assures accurate and intentional reciprocation of the knife assembly 200. Moreover, it is envisioned that the "pre-load" configuration of the torsion spring 75 acts as an automatic recoil of the knife assembly 200 to permit repeated reciprocation through the tissue as needed. As mentioned above, a plurality of gripping elements 71 is preferably incorporated atop the finger tab 72 and wing flanges 72a and 72b to enhance gripping of the finger tab 72.

Preferably, the trigger assembly 70 is initially prevented from firing due to the unique configuration of the distal end 63 of the link 65 which abuts against the finger tab 72 and "locks" the trigger assembly 70 prior to actuation of the handle assembly 30. Moreover, it is envisioned that the opposing jaw members 110 and 120 may be rotated and partially opened and closed without unlocking the trigger assembly 70 which, as can be appreciated, allows the user to grip and manipulate the tissue 420 without premature activation of the knife assembly 200. As mentioned below, only when the t-shaped end 93 of flange 92 is completely reciprocated within channel 54 and seated within a pre-defined catch basin 62 (explained below) will the distal end 63 of link 65 move into a position which will allow activation of the trigger assembly 70.

The operating features and relative movements of the internal working components of the forceps 10 are shown by phantom representation and directional arrows and are best illustrated in FIGS. 21–29. As mentioned above, when the forceps 10 is assembled a predefined channel 54 is formed within the cavity 52 of fixed handle 50. The channel 54 includes entrance pathway 53 and an exit pathway 58 for reciprocation of the flange 92 and the t-shaped end 93 therein. Once assembled, the two generally triangular-shaped members 57a and 57b are positioned in close abutment relative to one another and define track 59 disposed therebetween.

More particularly, FIGS. 21 and 22 show the initial actuation of handle 40 towards fixed handle 50 which causes the free end 93 of flange 92 to move generally proximally and upwardly along entrance pathway 53. During movement of the flange 92 along the entrance and exit pathways 53 and 58, respectively, the t-shaped end 93 rides along track 59 between the two triangular members 57a and 57b.

As the handle 40 is squeezed and flange 92 is incorporated into channel 54 of fixed handle 50, the cam link 36, through the mechanical advantage of the four-bar mechanical linkage, is rotated generally proximally about pivots 37 and 69 such that the cam piston 38 biases tab 25 which compresses spring 22 against flange 23 of the spring mount (FIG. 23). Simultaneously, the drive rod 32 is pulled proximally by the compression sleeve 27 which, in turn, causes cam pin 170 to move proximally within cam slots 172 and 174 and close the jaw members 110 and 120 relative to one another (FIG. 24). It is envisioned that channel 197 may be dimensioned slightly larger than needed to take into account any dimensional inconsistencies with respect to manufacturing tolerances of the various operating components of the end effector assembly 100 (FIG. 24)

It is envisioned that the utilization of a four-bar linkage will enable the user to selectively compress the coil spring 22 a specific distance which, in turn, imparts a specific load on the drive rod 32. The drive rod 32 load is converted to a torque about the jaw pivot 160 by way of cam pin 170. As a result, a specific closure force can be transmitted to the opposing jaw members 110 and 120. It is also contemplated, that window 340 disposed in the housing 20 may include graduations, visual markings or other indicia which provide feedback to the user during compression of the handle assembly 30. As can be appreciated, the user can thus selectively regulate the progressive closure forces applied to the tissue 420 to accomplish a particular purpose or achieve a particular result. For example, it is envisioned that the user may progressively open and close the jaw members 110 and 120 about the tissue without locking the flange 93 in the catch basin 62. The window 340 may include a specific visual indicator which relates to the proximal-most position of flange 93 prior to engagement within the catch basin 62.

Figure 4:
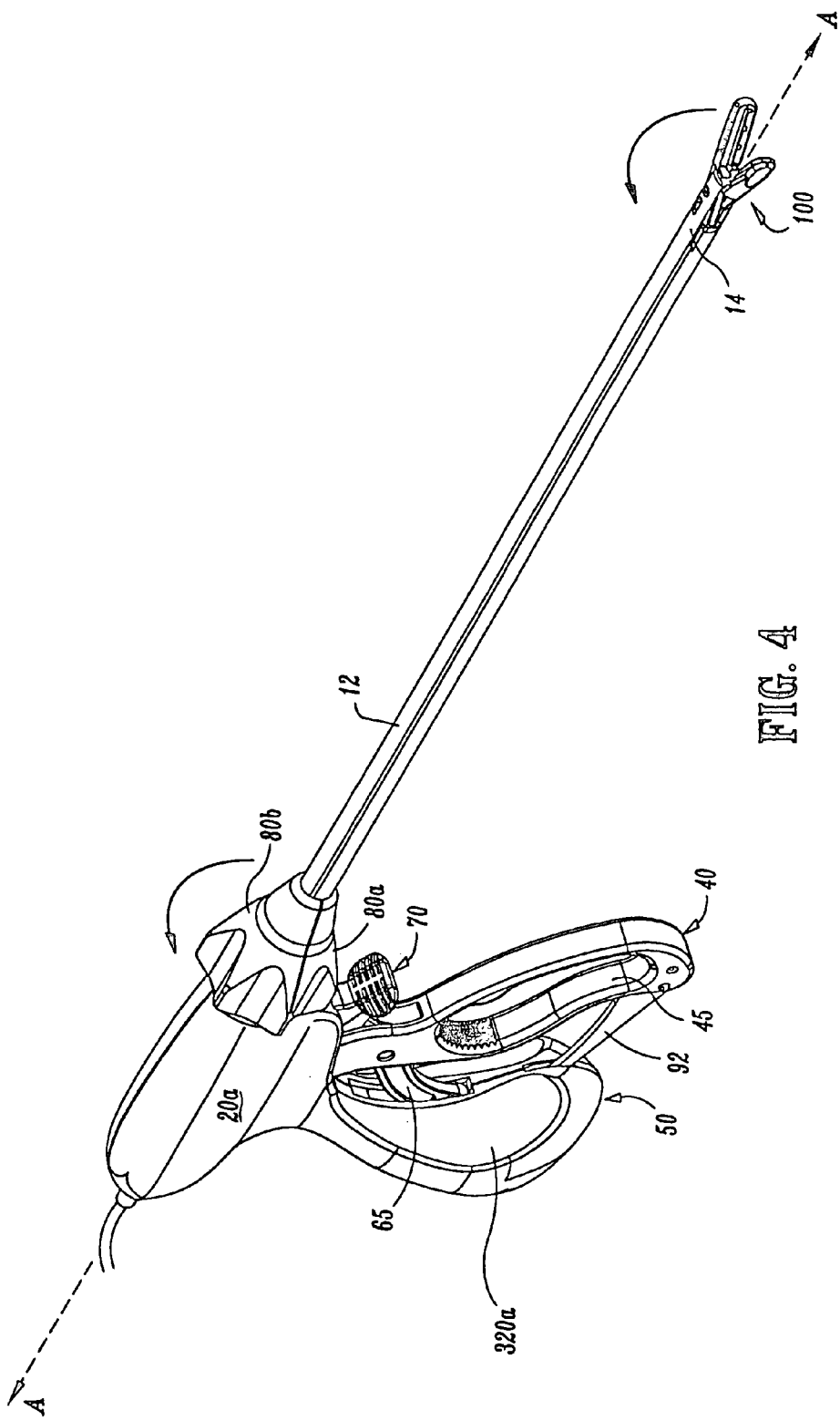
FIG. 4 is a right, perspective view of the forceps of FIG. 1 showing the rotation of the end effector assembly about a longitudinal axis "A"

As mentioned above, the jaw members 110 and 120 may be opened, closed and rotated to manipulate tissue 420 until sealing is desired without unlocking the trigger assembly 70. This enables the user to position and re-position the forceps 10 prior to activation and sealing. More particularly, as illustrated in FIG. 4, the end effector assembly 100 is rotatable about longitudinal axis "A" through rotation of the rotating assembly 80. As mentioned above, it is envisioned that the unique feed path of the cable leads 310a and 310b through the rotating assembly 80, along shaft 12 and, ultimately, through the jaw members 110 and 120 enable the user to rotate the end effector assembly 100 about 180 degrees in both the clockwise and counterclockwise direction without tangling or causing undue strain on the cable leads 310a and 310b. As can be appreciated, this facilitates the grasping and manipulation of tissue 420.

A series of stop members 150a–150c are preferably employed on the inner facing surfaces of the electrically conductive sealing surfaces 112 and 122 to facilitate gripping and manipulation of tissue and to define a gap "G" (FIG. 24) between opposing jaw members 110 and 120 during sealing and cutting of tissue. A detailed discussion of these and other envisioned stop members 150a–150c as well as various manufacturing and assembling processes for attaching and/or affixing the stop members 150a–150c to the electrically conductive sealing surfaces 112, 122 are described in commonly-assigned, co-pending U.S. application Ser. No. 10/471,818 entitled "VESSEL SEALER AND DIVIDER WITH NON-CONDUCTIVE STOP MEMBERS" by Dycus et al. which is hereby incorporated by reference in its entirety herein.

Once the desired position for the sealing site 425 is determined and the jaw members 110 and 120 are properly positioned, handle 40 may be compressed fully such that the t-shaped end 93 of flange 92 clears a predefined rail edge 61 located atop the triangular-shaped members 57a and 57b. Once end 93 clears edge 61, distal movement of the handle 40 and flange 92, i.e., release, is redirected by edge 61 into a catch basin 62 located within the exit pathway 58. More particularly, upon a slight reduction in the closing pressure of handle 40 against handle 50, the handle 40 returns slightly distally towards entrance pathway 53 but is re-directed towards exit pathway 58. At this point, the release or return pressure between the handles 40 and 50 which is attributable and directly proportional to the release pressure associated with the compression of the drive assembly 70 causes the end 93 of flange 92 to settle or lock within catch basin 62. Handle 40 is now secured in position within fixed handle 50 which, in turn, locks the jaw members 110 and 120 in a closed position against the tissue 420.

At this point the jaws members 100 and 120 are fully compressed about the tissue 420 (FIG. 26). Moreover, the forceps 10 is now ready for selective application of electrosurgical energy and subsequent separation of the tissue 420, i.e., as t-shaped end 93 seats within catch basin 62, link 65 moves into a position to permit activation of the trigger assembly 70 (FIGS. 21 and 29).

As the t-shaped end 93 of flange 92 becomes seated within catch basin 62, a proportional axial force on the drive rod 32 is maintained which, in turn, maintains a compressive force between opposing jaw members 110 and 120 against the tissue 420. It is envisioned that the end effector assembly 100 and/or the jaw members 110 and 120 may be dimensioned to off-load some of the excessive clamping forces to prevent mechanical failure of certain internal operating elements of the end effector 100.

As can be appreciated, the combination of the four-bar mechanical advantage along with the compressive force associated with the compression spring 22 facilitate and assure consistent, uniform and accurate closure pressure about the tissue 420.

By controlling the intensity, frequency and duration of the electrosurgical energy applied to the tissue 420, the user can either cauterize, coagulate/desiccate, seal and/or simply reduce or slow bleeding. As mentioned above, two mechanical factors play an important role in determining the resulting thickness of the sealed tissue and effectiveness of the seal 425, i.e., the pressure applied between opposing jaw members 110 and 120 and the gap distance "G" between the opposing sealing surfaces 112, 122 of the jaw members 110 and 120 during the sealing process. However, thickness of the resulting tissue seal 425 cannot be adequately controlled by force alone. In other words, too much force and the two jaw members 110 and 120 would touch and possibly short resulting in little energy traveling through the tissue 420 thus resulting in a bad tissue seal 425. Too little force and the seal 425 would be too thick.

Applying the correct force is also important for other reasons: to oppose the walls of the vessel; to reduce the tissue impedance to a low enough value that allows enough current through the tissue 420; and to overcome the forces of expansion during tissue heating in addition to contributing towards creating the required end tissue thickness which is an indication of a good seal 425.

Preferably, the electrically conductive sealing surfaces 112, 122 of the jaw members 110, 120, respectively, are relatively flat to avoid current concentrations at sharp edges and to avoid arcing between high points. In addition and due to the reaction force of the tissue 420 when engaged, jaw members 110 and 120 are preferably manufactured to resist bending. For example, the jaw members 110 and 120 may be tapered along the width thereof which is advantageous for two reasons: 1) the taper will apply constant pressure for a constant tissue thickness at parallel; 2) the thicker proximal portion of the jaw members 110 and 120 will resist bending due to the reaction force of the tissue 420.

As mentioned above, at least one jaw member, e.g., 110 may include a stop member, e.g., 150a, which limits the movement of the two opposing jaw members 110 and 120 relative to one another (FIGS. 6 and 7). Preferably, the stop member, e.g., 150a, extends from the sealing surface 112, 122 a predetermined distance according to the specific material properties (e.g., compressive strength, thermal expansion, etc.) to yield a consistent and accurate gap distance "G" during sealing (FIG. 24). Preferably, the gap distance between opposing sealing surfaces 112 and 122 during sealing ranges from about 0.001 inches to about 0.005 inches and, more preferably, between about 0.002 and about 0.003 inches.

Preferably, stop members 150a–150c are made from an insulative material, e.g., parylene, nylon and/or ceramic and are dimensioned to limit opposing movement of the jaw members 110 and 120 to within the above mentioned gap range. It is envisioned that the stop members 150a–150c may be disposed one or both of the jaw members 110 and 120 depending upon a particular purpose or to achieve a particular result. Many different configurations for the stop members 150a–150c are discussed in detail in commonly-assigned, co-pending U.S. application Ser. No. 10/471,818 entitled "VESSEL SEALER AND DIVIDER WITH NON-CONDUCTIVE STOP MEMBERS" by Dycus et al. which is hereby incorporated by reference in its entirety herein.

Preferably, the non-conductive stop members 150a–150c are molded onto the jaw members 110 and 120 (e.g., overmolding, injection molding, etc.), stamped onto the jaw members 110 and 120 or deposited (e.g., deposition) onto the jaw members 110 and 120. For example, one technique involves thermally spraying a ceramic material onto the surface of the jaw member 110 and 120 to form the stop members 150a–150c. Several thermal spraying techniques are contemplated which involve depositing a broad range of heat resistant and insulative materials on various surfaces to create stop members for controlling the gap distance between electrically conductive surfaces 112, 122. Other techniques for disposing the stop members 150a–150c on the electrically conductive surfaces 112 and 122 are also contemplated, e.g., slide-on, snap-on, adhesives, molds, etc.

Further, although it is preferable that the stop members 150a–150c protrude about 0.001 inches to about 0.005 and preferably about 0.002 inches to about 0.003 inches from the inner-facing surfaces 112, 122 of the jaw member 110 and 120, in some cases it may be preferable to have the stop members 150a–150c protrude more or less depending upon a particular purpose. For example, it is contemplated that the type of material used for the stop members 150a–150c and that material's ability to absorb the large compressive closure forces between jaw members 110 and 120 will vary and, therefore, the overall dimensions of the stop members 150a–150c may vary as well to produce the desired gap distance "G".

In other words, the compressive strength of the material along with the desired or ultimate gap distance "G" required (desirable) for effective sealing are parameters which are carefully considered when forming the stop members 150a–150c and one material may have to be dimensioned differently from another material to achieve the same gap distance or desired result. For example, the compressive strength of nylon is different from ceramic and, therefore, the nylon material may have to be dimensioned differently, e.g., thicker, to counteract the closing force of the opposing jaw members 110 and 120 and to achieve the same desired gap distance "G" when utilizing a ceramic stop member.

As best shown in FIGS. 27 and 28, as energy is being selectively transferred to the end effector assembly 100, across the jaw members 110 and 120 and through the tissue 420, a tissue seal 425 forms isolating two tissue halves 420a and 420b. At this point and with other known vessel sealing instruments, the user must remove and replace the forceps 10 with a cutting instrument (not shown) to divide the tissue halves 420a and 420b along the tissue seal 425. As can be appreciated, this is both time consuming and tedious and may result in inaccurate tissue division across the tissue seal 425 due to misalignment or misplacement of the cutting instrument along the ideal tissue cutting plane "B—B".

As explained in detail above, the present disclosure incorporates a knife assembly 200 which, when activated via the trigger assembly 70, progressively and selectively divides the tissue 420 along the ideal tissue plane "B—B" in an accurate and precise manner to effectively and reliably divide the tissue 420 into two sealed halves 420a and 420b (FIG. 31) with a tissue gap 430 therebetween. The reciprocating knife assembly 200 allows the user to quickly separate the tissue 420 immediately after sealing without substituting a cutting instrument through a cannula or trocar port 410. As can be appreciated, accurate sealing and dividing of tissue 420 is accomplished with the same forceps. It is envisioned that knife blade 205 may also be coupled to the same or an alternative electrosurgical energy source to facilitate separation of the tissue 420 along the tissue seal 425 (Not shown).

Moreover, it is envisioned that the angle of the blade tip 207 of the knife blade 205 may be dimensioned to provide more or less aggressive cutting angles depending upon a particular purpose. For example, the blade tip 207 may be positioned at an angle which reduces "tissue wisps" associated with cutting. More over, the blade tip 207 may be designed having different blade geometries such as serrated, notched, perforated, hollow, concave, convex etc. depending upon a particular purpose or to achieve a particular result.

Although it is envisioned that the blade tip 207 have a relatively sharp leading edge, it is also envisioned that the blade tip 207 may be substantially blunt or dull. More particularly, it is contemplated that the combination of the closure force between the jaw members 110 and 120 together with the uniquely designed stop members 150a–150c grip and hold the tissue firmly between the jaw members 110 and 120 to permit cutting of the tissue by blade tip 207 even if tip 207 is substantially blunt. As can be appreciated, designing the blade tip 207 blunt eliminates concerns relating to utilizing sharp objects with the surgical field.

Once the tissue 420 is divided into tissue halves 420a and 420b, the jaw members 110 and 120 may be opened by re-grasping the handle 40 as explained below. It is envisioned that the knife assembly 200 generally cuts in a progressive, uni-directional fashion (i.e., distally), however, it is contemplated that the knife blade may dimensioned to cut bi-directionally as well depending upon a particular purpose. For example, the force associated with the recoil of the trigger spring 75 may be utilized to with a second blade (not shown) which is designed to cut stray tissue wisps or dangling tissue upon recoil of the knife assembly.

Figure 32:
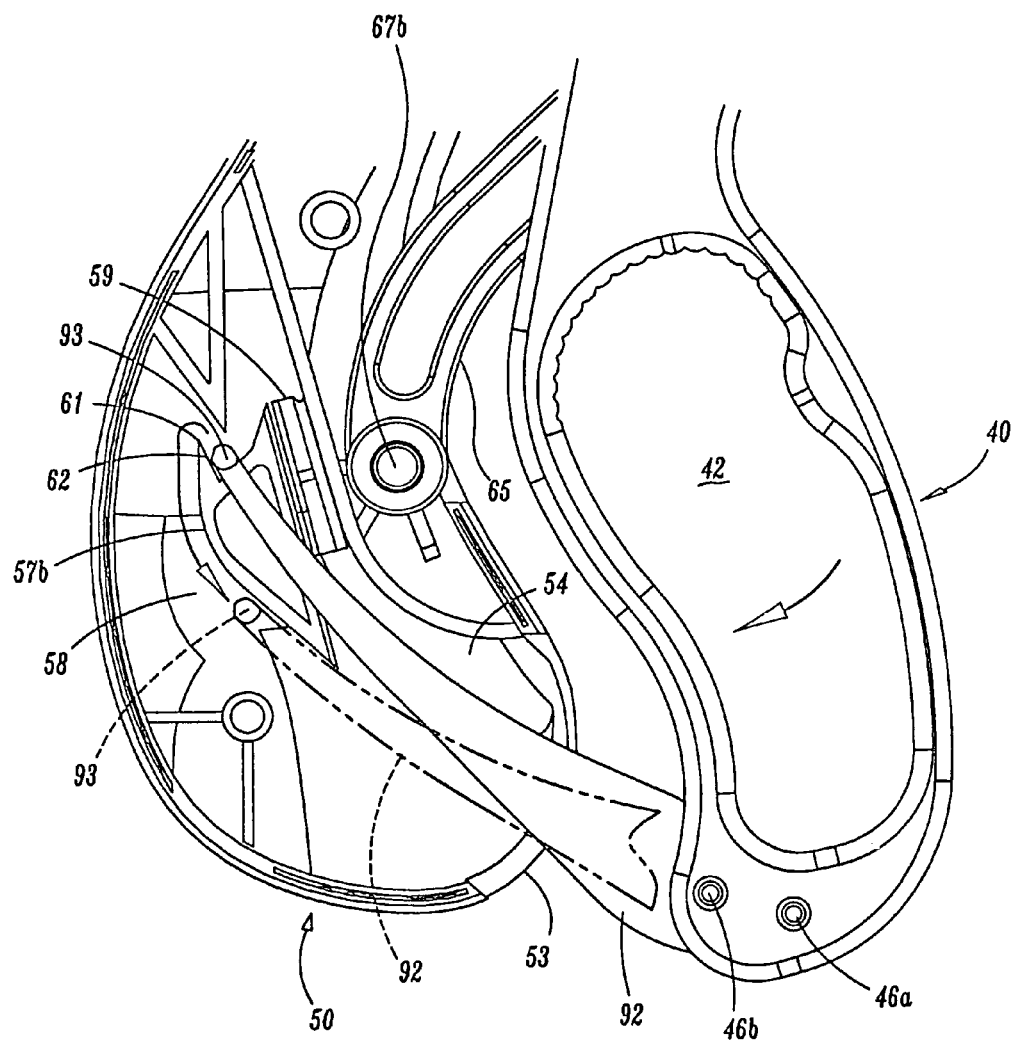
FIG. 32 is a greatly-enlarged, side view showing movement of the flange upon re-initiation of the handle assembly along a predefined exit path which, in turn, opens the opposing jaw members and releases the tubular vessel.

As best shown in FIG. 32, re-initiation or re-grasping of the handle 40 again moves t-shaped end 93 of flange 92 generally proximally along exit pathway 58 until end 93 clears a lip 61 disposed atop triangular-shaped members 57a, 57b along exit pathway 58. Once lip 61 is sufficiently cleared, handle 40 and flange 92 are fully and freely releasable from handle 50 along exit pathway 58 upon the reduction of grasping/gripping pressure which, in turn, returns the jaw members 110 and 120 to the open, pre-activated position.

From the foregoing and with reference to the various figure drawings, those skilled in the art will appreciate that certain modifications can also be made to the present disclosure without departing from the scope of the present disclosure. For example, it may be preferable to add other features to the forceps 10, e.g., an articulating assembly to axially displace the end effector assembly 100 relative to the elongated shaft 12.

It is also contemplated that the forceps 10 (and/or the electrosurgical generator used in connection with the forceps 10) may include a sensor or feedback mechanism (not shown) which automatically selects the appropriate amount of electrosurgical energy to effectively seal the particularly-sized tissue grasped between the jaw members 110 and 120. The sensor or feedback mechanism may also measure the impedance across the tissue during sealing and provide an indicator (visual and/or audible) that an effective seal has been created between the jaw members 110 and 120.

Moreover, it is contemplated that the trigger assembly 70 may include other types of recoil mechanism which are designed to accomplish the same purpose, e.g., gas-actuated recoil, electrically-actuated recoil (i.e., solenoid), etc. It is also envisioned that the forceps 10 may be used to dive/cut tissue without sealing. Alternatively, the knife assembly may be coupled to the same or alternate electrosurgical energy source to facilitate cutting of the tissue.

Although the figures depict the forceps 10 manipulating an isolated vessel 420, it is contemplated that the forceps 10 may be used with non-isolated vessels as well. Other cutting mechanisms are also contemplated to cut tissue 420 along the ideal tissue plane "B—B". For example, it is contemplated that one of the jaw members may include a cam-actuated blade member which is seated within one of the jaw members which, upon reciprocation of a cam member, is biased to cut tissue along a plane substantially perpendicular to the longitudinal axis "A".

Alternatively, a shape memory alloy (SMAs) may be employed to cut the tissue upon transformation from an austenitic state to a martenistic state with a change in temperature or stress. More particularly, SMAs are a family of alloys having anthropomorphic qualities of memory and trainability and are particularly well suited for use with medical instruments. SMAs have been applied to such items as actuators for control systems, steerable catheters and clamps. One of the most common SMAs is Nitinol which can retain shape memories for two different physical configurations and changes shape as a function of temperature. Recently, other SMAs have been developed based on copper, zinc and aluminum and have similar shape memory retaining features.

SMAs undergo a crystalline phase transition upon applied temperature and/or stress variations. A particularly useful attribute of SMAs is that after it is deformed by temperature/stress, it can completely recover its original shape on being returned to the original temperature. This transformation is referred to as a thermoelastic martenistic transformation.

Under normal conditions, the thermoelastic martenistic transformation occurs over a temperature range which varies with the composition of the alloy, itself, and the type of thermal-mechanical processing by which it was manufactured. In other words, the temperature at which a shape is "memorized" by an SMA is a function of the temperature at which the martensite and austenite crystals form in that particular alloy. For example, Nitinol alloys can be fabricated so that the shape memory effect will occur over a wide range of temperatures, e.g., $-270°$ to $+100°$ Celsius.

Although the jaw members as shown and described herein depict the jaw members movable in a pivotable manner relative to one another to grasp tissue therebetween, it is envisioned that the forceps may be designed such that the jaw members are mounted in any manner which move one or both jaw members from a first juxtaposed position relative to one another to second contact position against the tissue.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplications of a preferred embodiments. Those skilled in the art will envision other modifications within the scope and spirit of the claims appended hereto.

What is claimed is:

1. An electrosurgical instrument for performing at least one of sealing and dividing tissue, comprising:
   a housing having a shaft attached thereto, the shaft defining a longitudinal axis;
   a first jaw member movable relative to a second jaw member, the first jaw member attached to the shaft and being relatively movable from a first open position wherein the jaw members are disposed in spaced relation relative to one another to a second closed position wherein the jaw members cooperate to grasp tissue therebetween;
   a drive rod assembly operatively disposed within the housing which imparts movement of the jaw members between the first and second positions;
   a rotating assembly attached to the housing which rotates the jaw members about the longitudinal axis;
   a knife assembly attached to the housing which separates tissue grasped between the jaw members;
   a handle assembly attached to the housing which actuates the drive rod assembly, the handle assembly including a four-bar mechanical linkage which includes a handle and a cam-like piston which cooperate to impart a uniform closure pressure against tissue grasped between the jaw members;
   first and second electrical leads which connect the jaw members to a source of electrical energy such that the jaw members are capable of conducting energy through tissue held therebetween; and
   at least one of the first and second electrical leads including a slack loop disposed in the rotating assembly which permits rotation of the jaw members about the longitudinal axis.

2. An electrosurgical instrument according to claim 1 wherein the first and second jaw members are movable in a pivotable fashion relative to one another and the jaw members are rotatable substantially 360 degrees about the longitudinal axis.

3. An electrosurgical instrument according to claim 1 wherein the handle and the cam member of the four-bar mechanical linkage cooperate with a spring to create a uniform closure pressure against tissue grasped between the jaw members.

4. An electrosurgical instrument according to claim 1 wherein the handle is lockable within the housing to selectively lock the jaw members relative to one another.

5. An electrosurgical instrument according to claim 1 wherein the knife assembly is variable from a locked configuration to an unlocked configuration upon movement of the four-bar mechanical linkage.

6. An electrosurgical instrument according to claim 5 wherein the handle includes a flange which reciprocates into a channel having predefined internal dimensions disposed within the housing, the flange being dimensioned to cooperate with the predefined internal dimensions of the channel to selectively lock the jaw members relative to one another and unlock the knife assembly.

7. An electrosurgical instrument according to claim 5 wherein at least one jaw member includes a longitudinal channel at least partially defined therethrough which permits reciprocation of the knife assembly along an ideal cutting plane to separate tissue.

8. An electrosurgical instrument according to claim 1 wherein the first and second electrical leads are disposed within at least one channel defined in the outer periphery of the shaft.

9. An electrosurgical instrument according to claim 1 wherein the rotating assembly includes at least one mechanical interface which cooperates with a corresponding mechanical interface disposed on the housing to prevent overrotation of the jaw members.

10. An electrosurgical instrument according to claim 1 wherein the first electrical lead is disposed within a channel defined in the outer periphery of the shaft, the channel being oriented and dimensioned to facilitate introduction of the first electrical lead into the first jaw member.

* * * * *